(12) United States Patent
Honkonen et al.

(10) Patent No.: US 7,761,242 B2
(45) Date of Patent: Jul. 20, 2010

(54) METABONOMIC METHODS TO ASSESS HEALTH OF SKIN

(75) Inventors: Robert Stephen Honkonen, Cincinnati, OH (US); Wendy Qin, West Chester, OH (US); Hui Yang, Cincinnati, OH (US); David John Maltbie, Hamilton, OH (US); Bruce Ernest Tepper, Sycamore Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 553 days.

(21) Appl. No.: 11/707,670

(22) Filed: Feb. 16, 2007

(65) Prior Publication Data

US 2007/0202604 A1    Aug. 30, 2007

(51) Int. Cl.
*G06F 7/00*    (2006.01)

(52) U.S. Cl. .............................. 702/20; 702/19; 703/11; 707/102; 436/501

(58) Field of Classification Search ........................ None
See application file for complete search history.

(56) References Cited

U.S. PATENT DOCUMENTS

| | | | |
|---|---|---|---|
| 5,994,149 A | 11/1999 | Robinson et al. | |
| 6,447,463 B1 | 9/2002 | Borkowski | |
| 7,373,256 B2 * | 5/2008 | Nicholson et al. | 702/19 |

OTHER PUBLICATIONS

Wagner et al. Planta Medica 2004 vol. 70 pp. 897-903.*
J.K. Nicholson, J.C. Lindon and E. Holmes, Metabonomics: understanding the metabolic responses of living systems to pathophysiological stimuli via multivariate statistical analysis of biological NMR spectroscopic data, Xenobiotica, 1999, vol. 29, No. 11, 1181-1189.
J.K. Nicholson, John Connelly, J.C. Lindon, E. Holmes, Metabonomics: a platform for studying drug toxicity and gene function; Nature Reviews/Drug Discovery, vol. 1, Feb. 2002, pp. 153-161; 2002 Macmillan Magazines Ltd.
C.D. Eads, C.M Furnish, I. Noda, K.D. Juhlin, D.A. Cooper, S.W. Morrall, Molecular Factor Analysis Applied To Collections of NMR Spectra, Analytical Chemistry, vol. 76, No. 7, Apr. 1, 2004, 2004, American Chemical Society.
G.A. Webb, Annual Reports on NMR Spectroscopy, vol. 38, Academic Press, San Diego (1999).
J.C. Lindon, J.K. Nicholson, E. Holmes, J.R. Everett, Metabonomics: Metabolic Processes Studied by NMR Spectroscopy of Biofluids, Concepts in Magnetic Resonance, vol. 12(5), 289-230 (2000).
Junichi Koyama et al., "Free Amino-Acids of Stratum Corneum As A Biochemical Marker to Evaluate Dry Skin", Journal of the Society of Cosmetic Chemists, vol. 35, No. 4, Jul. 1984, pp. 183-196.
A. Weerheim et al., "Determination of Stratum Corneum Lipid Profile by tape Stripping in Combination with High-Performance Thin-Layer Chromatography", Archives of Dermatological Research, vol. 293, No. 4, Apr. 2001, pp. 191-199.
Mariko Hara et al., "Selectively Reduced Glycerol in Skin of Aquaporin-3-deficient Mice May Account for Impaired Skin Hydration, Elasticity, and Barrier Recovery", The Journal of Biological Chemistry, Nov. 29, 2002, vol. 277, No. 48, pp. 46616-46621.
International Search Report, PCT/IB2007/050633, mailed Jul. 10, 2007.

* cited by examiner

*Primary Examiner*—Mary K Zeman
(74) *Attorney, Agent, or Firm*—John G. Powell; Amy M. Foust

(57) ABSTRACT

The present invention relates to methods of assessing the health of skin. Biomarkers are used to evaluate skin samples. Using metabonomics approaches, samples taken from different skin sites or at different times during a treatment are used to diagnose skin conditions or to appraise various skin treatments for efficacy.

17 Claims, 21 Drawing Sheets

Front Thigh(1,2)

Intertriginous (3,4)

Upper Buttock (5,6)

Lower Buttock (7,8)

Back Thigh (9,10)

$^1$H Chemical Shift (ppm/TMS)

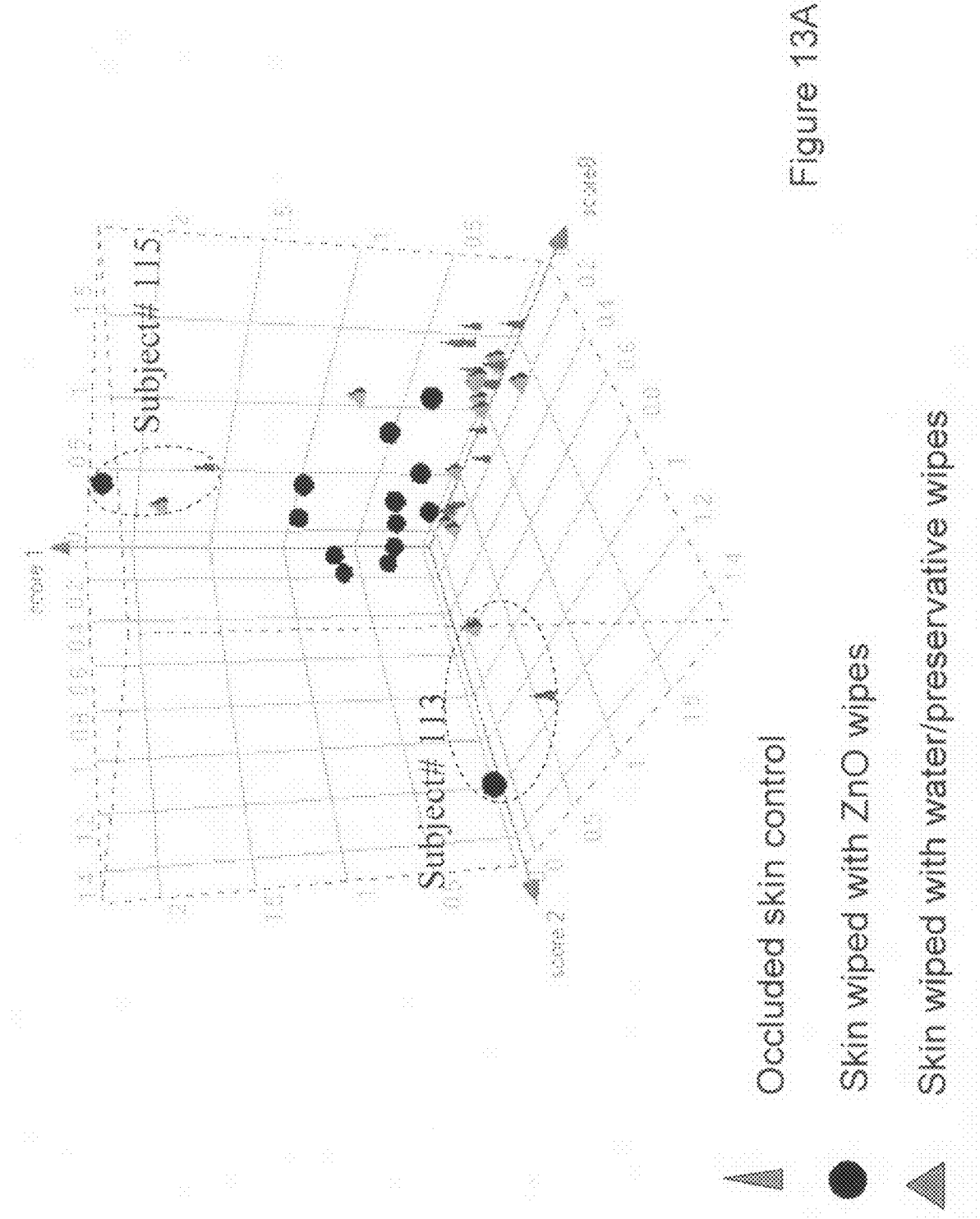

METABONOMIC METHODS TO ASSESS HEALTH OF SKIN

CROSS-REFERENCE TO RELATED APPLICATIONS

This application claims the benefit of U.S. application Ser. No. 11/362,627, filed on Feb. 27, 2006, the substance of which is incorporated herein by reference.

FIELD OF THE INVENTION

The present invention relates to methods of assessing the health of skin. More particularly, the present invention provides methods for evaluating skin using measurements of metabolites from skin samples. The present invention further provides methods for assessing the efficacy of treatments for skin conditions.

BACKGROUND OF THE INVENTION

Clinical and non-clinical scientific studies of biological responses, and in particular, dermatological responses, are hindered when current methods or devices cannot detect weak responses or distinguish among multiple causes for an observed response. Such studies are further hindered when the response being studied occurs with relatively low and unpredictable frequency among the general population.

Spectroscopic data of metabolites from biological samples are complex, and visual inspection can only yield a small amount of the information available. A different technique, coined metabonomics by Jeremy Nicholson and mirrored after genomics and proteomics, has been developed to extract the maximum information from the complex spectra measured. Specifically, metabonomics is a quantitative measurement of the dynamic multiparametric metabolic response of living systems to pathophysiological stimuli or genetic modification (Lindon et al., *Prog. NMR Spectrosc.*, 39:1 (2001)). What makes metabonomics potentially more powerful than either genomics or proteomics is that many disease states involve more than one gene or protein, but involve a finite number of metabolites. By studying spectroscopic data of small molecule metabolites from a biological sample, one can trace the levels of the metabolites of interest during the course of a disease state in comparison to a control sample. The dynamic and time-dependent profiles of the metabolites allow for the appraisal of treatments and, in some cases, can assist in diagnosis of a disease-state.

One particularly useful means of measuring metabolites in a biological sample is nuclear magnetic resonance (NMR). High field proton NMR spectra have been measured and compared for metabolite level differences between diseased subjects and control subjects, as well as for historical analyses of metabolite levels over a period of time for a disease. The spectra have been amassed in a database and can be used for comparison with future samples. Most applications of metabonomics have focused on blood and urine samples. There is now a large database of spectra of both urine and blood from subjects diagnosed with a wide range of diseases, such as the proprietary databases of Metabomatrix (London, UK), or annual reports such as, e.g., "Annual Reports on NMR SPECTROSCOPY" G. A. Webb, ed., *Academic Press*, volume 38: 1-88 (1999).

Little work has been done on the metabolites involved in skin conditions or on how those metabolites change during the course of a diseased or challenged state. Thus, there exists a need in the art to more clearly elucidate metabolites associated with skin conditions, and changes therein, and to provide methods of assessing efficacy of skin treatments. Such methods would be particularly useful where enhancing or ameliorating a response to a challenge is desirable. Methods of this type would also be useful when the response of interest needs to be studied under both highly controlled and poorly-controlled challenge scenarios.

SUMMARY OF THE INVENTION

The present invention allows for the assessment of skin conditions in a quantitative manner. The invention provides methods for assessing changes in skin conditions, comprising comparing biomarkers on challenged skin to biomarkers on control skin, wherein the comparison between the biomarkers indicates a change in skin condition. The invention further provides methods of assessing a change in skin condition, comprising isolating biomarkers from challenged skin and biomarkers from control skin, and comparing individual analyses of biomarkers from challenged skin to biomarkers from control skin. In certain cases, the biomarkers of challenged skin are monitored through time and/or across treatments as a means of assessing recovery of skin and/or efficacy of treatment. In certain cases, one of the biomarkers analyzed is urocanic acid. In one embodiment, the method of assessing biomarkers is carried out using NMR, mass spectrometry, liquid chromatography, capillary electrophoresis, other chromatographic techniques and/or combinations thereof.

Another aspect of the invention provides methods to assess a change in skin condition, comprising removing biomarkers from challenged skin and biomarkers from control skin with separate adhesive strips, extracting from the adhesive strips biomarkers from challenged skin and biomarkers from control skin, analyzing extracted biomarkers from challenged skin and biomarkers from control skin, and comparing results from the analysis, wherein the difference between the biomarkers of the challenged skin and the biomarkers of the control skin indicate a change in skin condition. In certain cases, one of the biomarkers analyzed is urocanic acid. In one embodiment, the analysis is performed using NMR, mass spectrometry, liquid chromatography, capillary electrophoresis, other chromatographic techniques and/or combinations thereof.

Another embodiment of the present invention provides methods to assess a change in skin condition wherein the skin condition is associated with a topical challenge, a therapeutic challenge, a prophylactic challenge, or a pathological challenge. In one aspect, the topical challenge is occlusion. Contemplated occlusions include without limitation those resulting from contact with clothing, injury dressing, diaper, adult incontinence products, feminine hygiene products, and/or a substance. Substances include human substances or foreign substances. Therapeutic, cosmetic, or prophylactic challenges contemplated include topical medicaments to alleviate or prevent skin diseases or disorders or cleansers for the skin. Topical medicaments include solutions, wipes, ointments, powders, creams, or lotions. Pathological challenges contemplated include bacterial infections, viral infections, and parasitic infections.

Another aspect of the present invention provides arrays of data which may be used as predictive models of the state of health of skin of an individual sample. These arrays of data may be assembled from analyses of skin samples of known skin health. The set of biomarkers of the sample of unknown skin health is analyzed and compared to the array of data for similarity to sets of biomarkers of samples of known skin health in order to predict the state of health of the unknown sample.

BRIEF DESCRIPTION OF THE FIGURES

FIG. 13A shows a three-dimensional scores plot of various skin samples, with outlier subjects separated.

DETAILED DESCRIPTION OF THE INVENTION

Figure 1A:
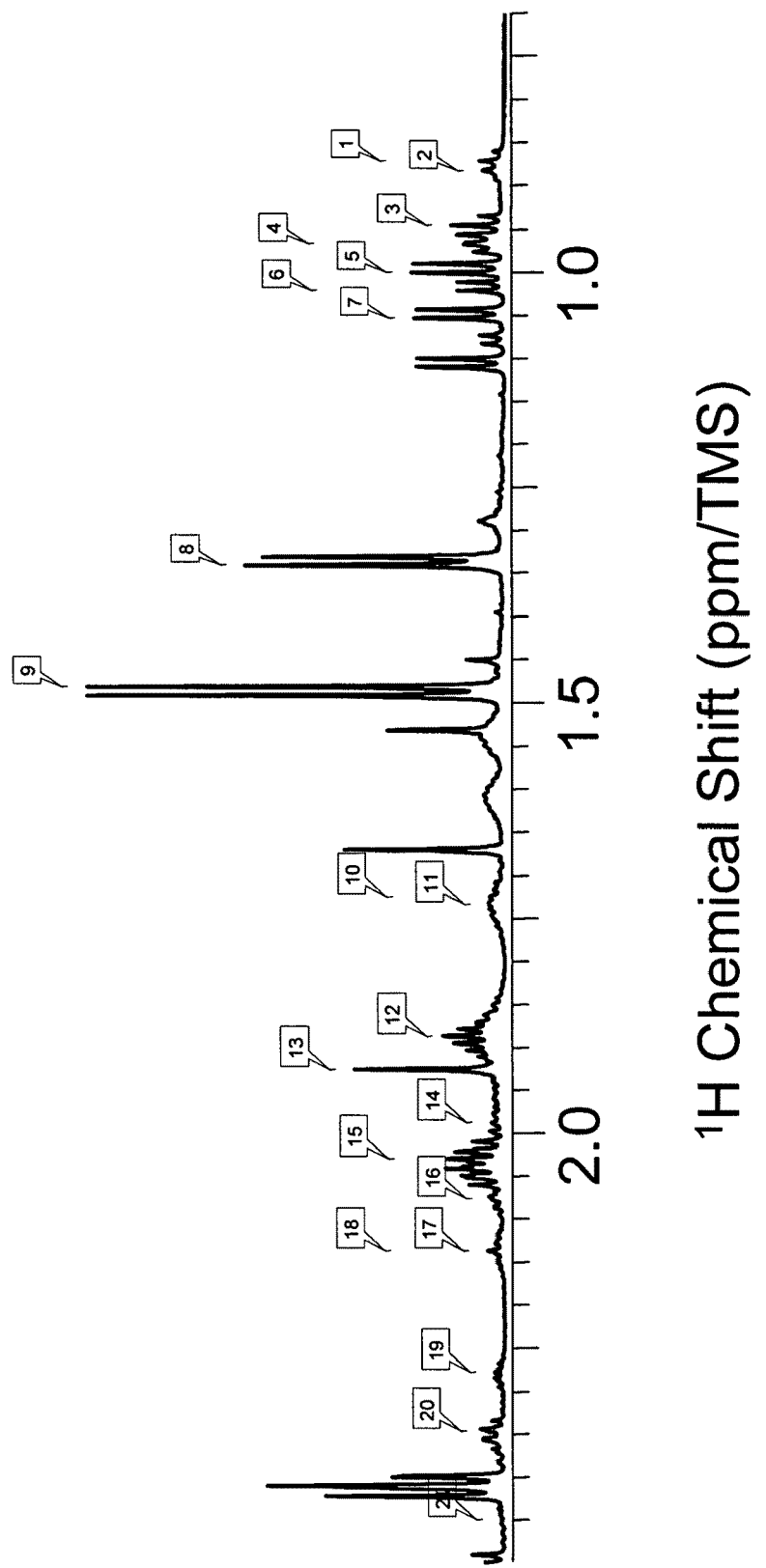
FIG. 1A shows a 700 MHz $^1$H NMR spectrum of an aqueous extraction of tape strip collected from occluded adult forearm skin. Spectrum corresponds to proton chemical shift range of about 0.5 to 2.5 ppm. All chemical shifts are reported relative to TMS.

Metabonomics approaches have previously been evaluated for biofluids such as blood and urine, and in biological samples such as tissues and tumors. Methods of the invention use metabonomics to analyze challenged skin samples. Comparison of data generated from challenged skin versus data from control, e.g., normal, healthy skin with respect to biomarkers on the skin surface, both from the same subject (to measure skin health over time or to compare treatment efficacies) or among different subjects, may allow for a better understanding of the means of skin challenge and the effectiveness of various skin treatments.

As used herein, "challenge" refers to the entity or process of provoking, moderating or otherwise influencing a physiological (including biochemical) activity by exposure under defined conditions to one or more physical, chemical or biological condition or action. In some cases, the challenge is a prophylactic or therapeutic challenge. Nonlimiting examples of such prophylactic or therapeutic challenges include topical medicaments and cleaners. Topical medicaments and cleaners include solutions, wipes, ointments, powders, creams, and lotions. These medicaments or cleansers can be of a type to alleviate or prevent skin disorders or conditions.

As used herein, "control skin" or "control" refers to any test site or study treatment used to establish a standard of comparison for judging experimental effects and/or the degree of variation in effects that occur during a study. Such controls include but are not limited to unchallenged skin, skin undergoing an alternate treatment, skin challenged by a different challenge, and the like.

As used herein, "biomarkers" are metabolites that are recoverable from skin and may be involved in the skin challenges of interest. These biomarkers may be identified in the spectral assessment of the samples, or they may be unknown but tracked over time or over a series of sample sites, to assess their presence and role in the conditions of interest. Unknown biomarkers that are determined to play a role in a resulting skin condition can be later identified using techniques well-known and routinely practiced in the art. Biomarkers, or metabolites, may be identified using the proprietary databases, such as those of Metabomatrix (London, UK), or comparing spectra to those published in annual reports such as, e.g., "Annual Reports on NMR SPECTROSCOPY" G. A. Webb, ed., *Academic Press*, volume 38: 1-88 (1999).

One complicating factor in assessing the state of skin is that there is a lack of homogeneity of skin samples due to the variation of skin type from different body locations, life style, diet, age, and even demographic differences. Individual differences have previously caused difficulties in predicting outcomes of clinical studies which rely only on visual grading and non-specific measurements such as Trans-epidermal water loss (TEWL). Further, skin samples are subject to a variety of environmental contaminations that can complicate analysis. In trying to remove these environmental contaminants with conventional approaches, one can alter the levels of metabolites in the skin sample and skew the spectroscopic profile of the sample. The metabonomic approach, as a holistic approach for metabolite analysis, may be able to isolate the differences and even identify the metabolites that are responsible for the individual variations.

Metabonomic assessment can be performed on one subject for comparison of metabolite levels in different skin sites or at different skin depths, or among different subjects with different skin types or other individual factors. These assessments bring insight into the way that metabolites at different skin sites or different skin types can point to certain skin challenges, and indicate the effectiveness of a skin treatment for one skin type or one skin challenge against a different one. Control of the skin environment is one way to ensure that samples taken from subjects are a true assessment of the skin metabolites due to particular challenges.

Factors that can affect the biomarkers detected from samples include skin challenges, skin microflora, metabolism over time, depth of skin sampled, and the like. In certain instances, the level of a metabolite may increase as the length of time between cleaning increases. This trend may be opposite to a metabolite gradient that decreases in skin depth according to depth profiling by ten consecutive samples taken at the same site. Thus, samples taken from a subject with challenged skin may show a different profile of metabolites than that of the same subject after treatment such as water washing or with a skin cleaning product. In this respect, the metabonomic approach provides an understanding of the impact on the methods available for substantiating a particular product's effectiveness versus that of a competing product.

Skin challenges of interest in the methods defined herein can be of a physical, chemical, or biological nature. Examples of physical challenges include, but are not limited to heat, cold, humidity, desiccation, radiant energy, dark, friction, abrasion, lubrication, electric or magnetic energy, pressure, vacuum, visual images such as tattoos, occlusion, and sound. Physical challenges include those that can arise from direct or indirect contact with an individual's skin with, including for example and without limitation diapers, condoms, injury dressings, feminine care products, bandages, clothing, acute or prolonged compression, trauma and/or abrasion, and the like. In some cases, physical challenges occur from reduced breathability of the skin due to these contacts. Some examples of chemical challenges include any element of the periodic table or compositions of those elements including, but not limited to organic and inorganic acids and bases or conditions caused by their presence in aqueous and/or non-aqueous systems, surfactants, metals and complexes thereof, salts, proteins, lipids, fats, carbohydrates, vitamins, polymers, pharmaceuticals, feces, urine, perspiration, hair, blood, nasal discharge, saliva, tears, ear wax, extracts, and enzyme digests. Some examples of biological challenges include, but are not limited to microbials, cells, viruses, bacteria, fungi, parasites, and/or other living entities including eukaryotes which directly induce a range of responses and/or indirectly are responsible for responses when they are vectors for the transmission of biological challenges. Biological challenges also include those which arise endogenously, including conditions such as from metabolic, genetic, dietary, and/or autoimmune disorders. Any challenges to the body that causes a skin change in biomarker presentation can be evaluated using methods of the present invention. Thus, the methods of the invention may be powerful tools in screening potential new products for their breathability and skin benefits. These methods may indicate promising uses for evaluating product efficacy. In addition, these approaches can be utilized in appropriate clinical study designs to assess the kinetics of skin recovery or for evaluating a person's health status, e.g. a prematurely born baby. The methods may allow for metabolites responsible for the separation of skin treatments or conditions to be identified in further analysis.

Methods of the invention are useful for a variety of assessments of skin conditions. In one aspect, severity of a skin condition can be evaluated based on a change, either an increase or decrease, in the level of one or more specific biomarkers associated with a specific challenge. In certain instances, severity of a challenge can also be assessed by identifying a change in a biomarker expression pattern known to follow a specific challenge. For example, a specific challenge may give rise to a specific biomarker expression pattern that is replaced, in one or more phases, with one or more specific expression patterns as the resulting condition deteriorates.

In another aspect, an improvement in skin condition can be assessed wherein a specific biomarker expression pattern associated with a specific challenge is first identified and subsequently observed to move closer to the biomarker expression pattern observed to be associated with control, or normal skin. Such an assessment may simply follow a change in biomarker presentation following removal of the challenge or may follow therapeutic (after challenge) or prophylactic (prior to challenge) intervention. Accordingly, assessment of the efficacy of particular skin treatments is one aspect of the present invention. In certain cases, assessment of the efficacy of treatment or the state of health of skin involves comparing time point samples from the same subject.

In methods of the invention, any of a number of techniques for obtaining a sample of skin biomarkers can be employed. In various aspects, mechanical scraping, swabbing and/or direct elution, pressure blotting, electric transfer, or the like may be employed. In another aspect, "tape-stripping" is utilized. As used herein, "tape-stripping" refers to the act of applying a material of known adhesive properties to skin in a prescribed manner and removing that material for the purposes of subjecting the skin to a physical challenge. Adhesive strips useful for tape-stripping, which need not specifically be in a tape format, include adhesive tapes such as D-squame™ and Sebutape™ (CuDerm Corporation, Dallas, Tex.) or Blenderm™ and ScotchTape™ (3M Company, St. Paul, Minn.), and hydrogels such as Hypan™ (Hymedix International, Inc., Dayton, N.J.), and other types of materials with adhesive properties such as glues, gums, and resins.

Regardless of the method used for obtaining a sample of skin biomarkers presented on the skin to be analyzed, in most instances the biomarkers are removed from the device or liquid used to obtain the sample and processed in such a manner that allows for assessment of the biomarkers. In general, the chosen method of analysis will dictate how the biomarker sample is processed, such processing techniques being well known in the art.

Spectral measurements are best suited for metabonomics when they allow for the separation of signals due to different metabolites. High resolution NMR is one means for measuring small molecule metabolites in a biological sample. Other means for measurement include mass spectrometry (MS), capillary electrophoresis (CE), liquid chromatography (LC), and combinations thereof. All of the preceding analytical methods have some method of extricating different metabolite data points. Use of NMR for metabonomics permits a wide range of metabolites to be quantified simultaneously with simple sample preparation. Additionally, NMR is powerful and sensitive enough to detect sub-clinical skin changes, i.e., before skin changes become visible, at a molecular level in a non-subjective/non-biased fashion from tape strips. For example, the NMR approach may provide a tool to measure skin impact of occlusion and wipes cleaning effects quantitatively. In addition, this approach could be used for monitoring metabolite recovery process in skin, an important parameter of skin benefits. Accordingly, the NMR approach for analyzing skin benefits can be used for product skin benefits evaluation: (1) by measuring occlusion effect for breath-ability of diaper, (2) by determining wipe cleaning effect for lotion wipes urine and BM cleaning efficacy, and (3) by monitoring the process of skin metabolites shifting back to normal population after wipe cleaning to demonstrate skin health benefit. Monitoring metabolite recovery process in skin after cleaning can also be a useful approach for demonstrating skin benefits of many beauty care products and may also predict skin health status such as for prematurely born babies whose skin function is critical for their survival.

NMR spectroscopy is based on the behavior of atoms placed in a static external magnetic field. Atomic nuclei possessing a property known as spin that is not equal to zero can give rise to NMR signals. Nuclei possessing this property include $^1$H, $^{13}$C, $^{15}$N and $^{31}$P. Since protons are present in almost all metabolites in body fluids, an $^1$H NMR spectrum allows the simultaneous detection and quantification of thousands of proton-containing, low-molecular weight species within a biological matrix, resulting in the generation of an endogenous profile that may be altered in disease to provide a characteristic "fingerprint" (Nicholson, J. K., Lindon, J. C., and Holmes, E. *Xenobiotica*, 29: 1181-1189 (1999); Lindon, J. C., Nicholson, J. K., and Everett, J. R. *Annu. Rep. NMR Spectrosc.*, 38: 1-88 (1999); Lindon, J. C., Nicholson, J. K., Holmes, E., and Everett, J. R., *Concepts Magn. Reson.*, 12: 289-320 (2000); and Nicholson, J. K., Connelly, J., Lindon, J. C., and Holmes, E. *Nat. Rev. Drug Discov.*, 1: 153-161, (2002)). A range of NMR strategies has also been developed for structure elucidation of metabolites in biofluids.

Pattern Recognition (PR) is essential for NMR spectra of biologic samples because the samples are extremely complex, and much information can be lost even in rigorous statistical analysis of quantitative data as the essential diagnostic parameters are carried in the overall patterns of the spectra. Therefore, in order to reduce NMR data complexity and facilitate analysis, data-reduction followed by chemometric methods, such as Principal Components Analysis (PCA) and Partial Least Squares-Discriminant Analysis (PLS-DA), can be applied. Various other treatments of the data can be used as appropriate, and can be easily determined by one of skill in the art.

The intrinsic accuracy of NMR provides a distinct advantage when applying pattern recognition techniques. The multivariate nature of the NMR data means that classification of samples is possible using a combination of descriptors even when one descriptor is not sufficient, because of the inherently low analytical variation in the data. All biological fluids and tissues have their own characteristic physico-chemical properties, and these affect the types of NMR experiment that may be usefully employed. One major advantage of using NMR spectroscopy to study complex biomixtures is that measurements can often be made with minimal sample preparation and a detailed analytical profile can be obtained on the whole biological sample. Sample volumes are small, typically 0.3 to 0.5 mL for standard probes, and as low as 3 µL for microprobes. Acquisition of simple NMR spectra is rapid and efficient using flow-injection technology. It is usually necessary to suppress the water NMR resonance.

In all cases the analytical problem usually involves the detection of "trace" amounts of analytes in a very complex matrix of potential interferences. It is, therefore, critical to choose a suitable analytical technique for the particular class of analyte of interest in the particular sample. High resolution NMR spectroscopy (in particular $^1$H NMR) was found to be particularly appropriate. The main advantages of using $^1$H NMR spectroscopy are the speed, the requirement for minimal sample preparation, and the fact that it provides a non-selective detector for all metabolites in the sample regardless of their structural type, provided only that they are present above the detection limit of the NMR experiment and that they contain non-exchangeable hydrogen atoms.

In one aspect, NMR studies of samples are performed at the highest magnetic field available to obtain maximal dispersion and sensitivity. In one embodiment, $^1$H NMR studies are performed at 500 MHz or greater. With every new increase in available spectrometer frequency the number of resonances that can be resolved in a sample increases, and although these increases have the effect of solving some assignment problems, they also pose new ones. Furthermore, there are still important problems of spectral interpretation that arise due to compartmentation and binding of small molecules in the organized macromolecular domains that exist in some samples. All of this complexity need not reduce the diagnostic capabilities and potential of the technique, but demonstrates the problems of biological variation and the influence of variation on diagnostic certainty.

The information content of the sample spectra is very high and the complete assignment of the $^1$H NMR spectrum is not always possible (even using 900 MHz NMR spectroscopy). However, the assignment problems vary between sample types. Those metabolites present close to the limits of detection for 1-dimensional (1D) NMR spectroscopy (typically about 100 nM at 800 MHz) pose NMR spectral assignment problems. In absolute terms, the detection limit may be about 4 nmol, e.g., 1 µg of a 250 g/mol compound in a 0.5 mL sample volume. Even at the present level of technology in NMR, it is not yet possible to detect many important biochemical substances (e.g. hormones, some proteins, nucleic acids) in a sample because of problems with sensitivity, line widths, dispersion and dynamic range and this area of research will continue to be technology-limited. In addition, the collection of NMR spectra of biological samples may be complicated by the relative water intensity, sample viscosity, protein content, lipid content, and low molecular weight peak overlap.

Usually in order to assign $^1$H NMR spectra, comparison is made with spectra of authentic materials and/or by standard addition of an authentic reference standard to the sample. Additional confirmation of assignments is usually sought from the application of other NMR methods, including, for example, 2-dimensional (2D) NMR methods, particularly COSY (correlation spectroscopy), TOCSY (total correlation spectroscopy), inverse-detected heteronuclear correlation methods such as HMBC (heteronuclear multiple bond correlation), HSQC (heteronuclear single quantum coherence), and HMQC (heteronuclear multiple quantum coherence), 2D J-resolved (JRES) methods, spin-echo methods, relaxation editing, diffusion editing (e.g., both 1D NMR and 2D NMR such as diffusion-edited TOCSY), and multiple quantum filtering.

All of these factors contribute to the importance of using statistical analysis to assess the NMR data and reduce the complexity of the data sets. In general, the use of PR algorithms allows the identification, and, with some methods, the interpretation of some non-random behavior in a complex system which can be obscured by noise or random variations in the parameters defining the system. Also, the number of parameters used can be very large such that visualization of the regularities, which for the human brain is best in no more than three dimensions, can be difficult. Usually the number of measured descriptors is much greater than three and so simple scatter plots cannot be used to visualize any similarity between samples. In the context of the methods described herein, PR is the use of multivariate statistics, both parametric and non-parametric, to analyze spectroscopic data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. The other approach is termed "supervised" whereby a training set of samples with known class or outcome is used to produce a mathematical model and this is then evaluated with independent validation data sets.

Unsupervised PR methods are used to analyze data without reference to any other independent knowledge, for example, without regard to the identity or nature of a xenobiotic or its mode of action. Examples of unsupervised pattern recognition methods include principal component analysis (PCA), hierarchical cluster analysis (HCA), and non-linear mapping (NLM).

One useful and easily applied unsupervised PR technique is principal components analysis (PCA). Principal components (PCs) are new variables created from linear combinations of the starting variables with appropriate weighting coefficients. The properties of these PCs are such that (i) each PC is orthogonal to (uncorrelated with) all other PCs, and (ii) the first PC contains the largest part of the variance of the data set (information content) with subsequent PCs containing correspondingly smaller amounts of variance.

PCA, a dimension reduction technique, takes m objects or samples, each described by values in k dimensions (descriptor vectors), and extracts a set of eigenvectors, which are linear combinations of the descriptor vectors. The eigenvectors and eigenvalues are obtained by diagonalization of the covariance matrix of the data. The eigenvectors can be thought of as a new set of orthogonal plotting axes, called principal components (PCs). The extraction of the systematic variations in the data is accomplished by projection and modeling of variance and covariance structure of the data matrix. The primary axis is a single eigenvector describing the largest variation in the data and is termed principal component one (PC1). Subsequent PCs, ranked by decreasing eigenvalue, describe successively less variability. The variation in the data that has not been described by the PCs is called residual variance and signifies how well the model fits the data. The projections of the descriptor vectors onto the PCs are defined as scores, which reveal the relationships between the samples or objects. In a graphical representation (a "scores plot" or eigenvector projection), objects or samples having similar descriptor vectors will group together in clusters. Another graphical representation is called a loadings plot, which connects the PCs to the individual descriptor vectors and displays both the importance of each descriptor vector to the interpretation of a PC and the relationship among descriptor vectors in that PC. In fact, a loading value is simply the cosine of the angle which the original descriptor vector makes with the PC. Descriptor vectors which fall close to the origin in this plot carry little information in the PC, while descriptor vectors distant from the origin (high loading) are important in interpretation.

Thus a plot of the first two or three PC scores gives the "best" representation, in terms of information content, of the data set in two or three dimensions, respectively. A plot of the first two principal component scores, PC1 and PC2 provides the maximum information content of the data in two dimensions. Such PC maps can be used to visualize inherent clustering behavior, for example, for drugs and toxins based on similarity of their metabonomic responses and hence mechanism of action. Of course, the clustering information might be in lower PCs and these have to be examined also. The PC loadings where each point represents one variable are used to detect those variables, or spectral readings in the case of a complex NMR spectrum, responsible for any separation of samples into clusters. After PCA of NMR spectral data, the molecules responsible for any separation in the data can then be characterized using 2-D NMR analysis or hyphenated separation techniques, such as LC, MS or CE (LC-NMR, MS-NMR, or CE-NMR).

Hierarchical Cluster Analysis, another unsupervised pattern recognition method, permits the grouping of data points which are similar by virtue of being "near" one another in some multidimensional space. Individual data points may be, for example, the signal intensities for particular assigned peaks in an NMR spectrum. A "similarity matrix," S, is constructed with elements $s_{ij}=1-r_{ij}/r_{ij}^{max}$, where $r_{ij}$ is the interpoint distance between points i and j (e.g., Euclidean interpoint distance), and $r_{ij}^{max}$ is the largest interpoint distance for all points. The most distant pair of points will have $s_{ij}$ equal to 0, since $r_{ij}$ then equals $r_{ij}^{max}$. Conversely, the closest pair of points will have the largest $s_{ij}$. For two identical points, $s_{ij}$ is 1.

The similarity matrix is scanned for the closest pair of points. The pair of points are reported with their separation distance, and then the two points are deleted and replaced with a single combined point. The process is then repeated iteratively until only one point remains. A number of different methods may be used to determine how two clusters will be joined, including the nearest neighbor method (also known as the single link method), the furthest neighbor method, and the centroid method (including centroid link, incremental link, median link, group average link, and flexible link variations).

The reported connectivities are then plotted as a dendrogram (a treelike chart which allows visualization of clustering), showing sample-sample connectivities versus increasing separation distance (or equivalently, versus decreasing similarity). The dendrogram has the property in which the branch lengths are proportional to the distances between the various clusters and hence the length of the branches linking one sample to the next is a measure of their similarity. In this way, similar data points may be identified algorithmically.

Non-linear mapping (NLM) is a simple concept which involves calculation of the distances between all of the points in the original k dimensions. This is followed by construction of a map of points in 2 or 3 dimensions where the sample points are placed in random positions or at values determined by a prior principal components analysis. The least squares criterion is used to move the sample points in the lower dimension map to fit the inter-point distances in the lower dimension space to those in the k dimensional space. Non-linear mapping is therefore an approximation to the true interpoint distances, but points close in k-dimensional space should also be close in 2 or 3 dimensional space.

The statistical analysis may comprise multivariate analysis, in particular by a partial least squares (PLS) method on the group of control samples. This produces a calibration data set, e.g. a set of metabolite scores or other factor scores from the control data. The PLS method makes it possible to establish a regression model between at least one estimated variable said to be dependent or latent, and variables that are said to be independent or manifest and that explain the variations in the latent variable.

"Supervised" PR methods may be appropriate when class membership is known for a set of observations. For such data sets, PCA uncovers the directions in multivariate space that represent the largest sources of variation. The maximum variation defined by these PCs does not necessarily coincide with the maximum separation directions among the classes. Instead, it may be that other directions are more pertinent for discriminating among classes of observations. Partial least squares discriminant analysis (PLS-DA) makes it possible to accomplish a rotation of the projection to give latent variables that focus on class separation. This method offers a convenient way to explicitly take into account the class membership of observations. Thus, PLS-DA develops a model that separates classes of observations on basis of their original x-variables. This model is based on a training set of observations with known class membership.

Molecular Factor Analysis (MFA) is a set of NMR data processing tools developed to identify and quantify the components of complex mixtures based on NMR spectra. The input is a set of NMR spectra of the mixtures. First, the data is reduced using singular value decomposition. The results are a set of principal component eigenspectra that contain enough information to reconstruct component spectra. However, the mathematical analysis that leads to principal components does not take into consideration the physical or chemical knowledge about the nature of NMR spectra, such as, e.g., all peaks in an NMR spectrum must be positive, all concentrations must be positive, and Beer's law must be obeyed. MFA algorithms allow one to find n different combinations of the n principal component eigenspectra that conform to all these facts so as to extract meaningful spectroscopic information from large NMR data sets. (Eads et al., *Analytical Chem* 76(7): 1982-1990 (2004))

The methods described herein, which employ pattern recognition techniques, permit identification of that NMR peak intensity which is related to the condition under study, even though only a small part of the variance in a spectral region may be related to the condition under study. The identification power is enhanced by the application of data filtering techniques (e.g., orthogonal signal correction, OSC) which can lower the influence of regions with variance unrelated to the condition of interest. Actual identification of the molecular biomarkers contributing to significant regions is carried out by reexamination of the original NMR spectra and could involve additional NMR spectroscopic experiments such as 2-dimensional NMR spectroscopy; separation of putative substances and their identification using HPLC-NMR-MS or other analytical combination techniques; addition of authentic substance to the sample and re-measuring the NMR spectrum, checking for coincidence of NMR peaks, etc.

Furthermore, the methods can be applied to achieve classification into multiple categories on the basis of a single dataset, for example, an NMR spectrum for a single sample. Due to the very high data density of the input dataset, the analysis method can separately (i.e., in parallel) or sequentially (i.e., in series) perform multiple classifications. For example, a single skin sample could be used to determine (e.g., diagnose) the presence or absence of several, or indeed, many, conditions or diseases.

Figure 9:
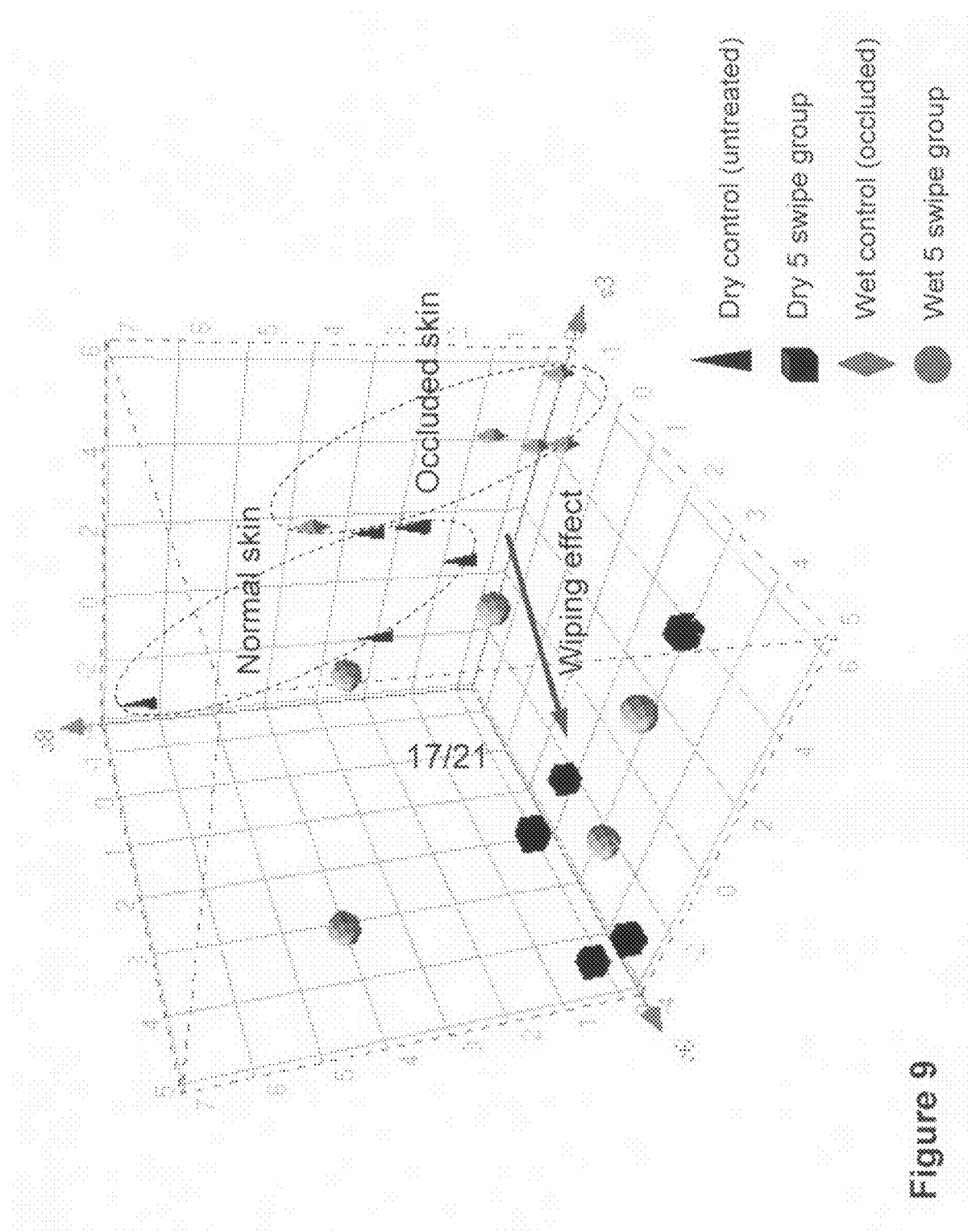
FIG. 9 shows a three-dimensional scores plot of skin in different states: untreated normal, occluded and wipe-cleaned.

Appropriate PR techniques can generate models from a well defined training set. These models can then be used to classify unknown samples with a single $^1$H NMR spectrum. For example, a single skin sample could be used to determine (e.g., diagnose) the presence or absence of a certain skin condition or disease. In one aspect, therefore, an assembly of data is provided as a predictive means for assessing the state of skin of individual samples. This assembly is generated by the collection of skin biomarker samples in a variety of skin states (e.g., healthy, occluded, soiled, and cleaned). Biomarkers in each skin sample are measured using an analytical technique, such as NMR, HPLC, mass spectrometry, and the like, to determine the presence (or absence) of biomarkers, and PR techniques are employed to generate scores of various factors, or biomarkers, for each sample. An array of scores for individual biomarkers can be assembled from the score analyses of the skin samples. Because the skin biomarker samples are from skin of a known state (e.g., healthy, occluded, soiled, and cleaned), the combination of scores can be tracked to identify partitioned sections of the array which are indicative of individual skin states. For example, FIG. 9 shows a 3D scores plot and the grouping of skin samples by skin state. Once the partitions of the array are identified, the array can be used as a predictive tool for assessing individual skin samples of unknown condition. Analysis of biomarkers in any skin sample to create scores allows for the skin sample to be "plotted" into this array and predict its skin state. In some embodiments, the array may be further partitioned within a skin state to specific, e.g., diseases, challenges, or treatments. This comparison to the arrayed data, or model, allows for the diagnosis of a skin challenge, comparison of different treatments for a challenge, assessment of the effect of a contact challenge on the state of skin, and other types of comparisons between skin samples and conditions.

Additional aspects and details of the invention will be apparent from the following examples, which are intended to be illustrative rather than limiting.

EXAMPLES

Example 1

Normal vs. Occluded Skin

Occlusion induced skin changes may not be easily or reproducibly evaluated by visual grading. Furthermore, the visual grading will not provide critical information needed in order to understand and predict skin responses to certain treatments and to create measures to maintain or promote skin health. Sensitive techniques with high resolving power are needed to analyze skin at the molecular level.

Skin samples are collected from a clinical study that is carried out on adult arms. Each arm has two of the three sites assigned to treatment with either a fully occlusive patch (Saran Wrap®) or a patch prepared from a more breathable material, such as a Hytrel film (Dupont), with a low moisture vapor transmission rate (MVTR) of about 350 g/m$^2$/24 hours. The third site is a non-occluded control. The area of the skin where a patch will be placed is marked. The treatment patch is placed on the skin and secured to the skin with Tegaderm tape (3M). Each patch site is patched for approximately 24 hrs with a 4×5 cm$^2$ patch made of one of the test materials. Some sites are repatched for 2 additional 24 hr periods. Skin samples are collected by D-Squame™ tape stripping and stored at or below −20° C. until use. Each skin tape is extracted by placing a single tape in a glass vial and adding 200 µL D$_2$O. The tissue side of the strip should be face down in the vial for good contact with the solvent. The vial is sonicated for 15-30 min. and vortexed for 30 sec. The extracts are transferred to sample tubes for $^1$H NMR measurement.

Figure 1B:
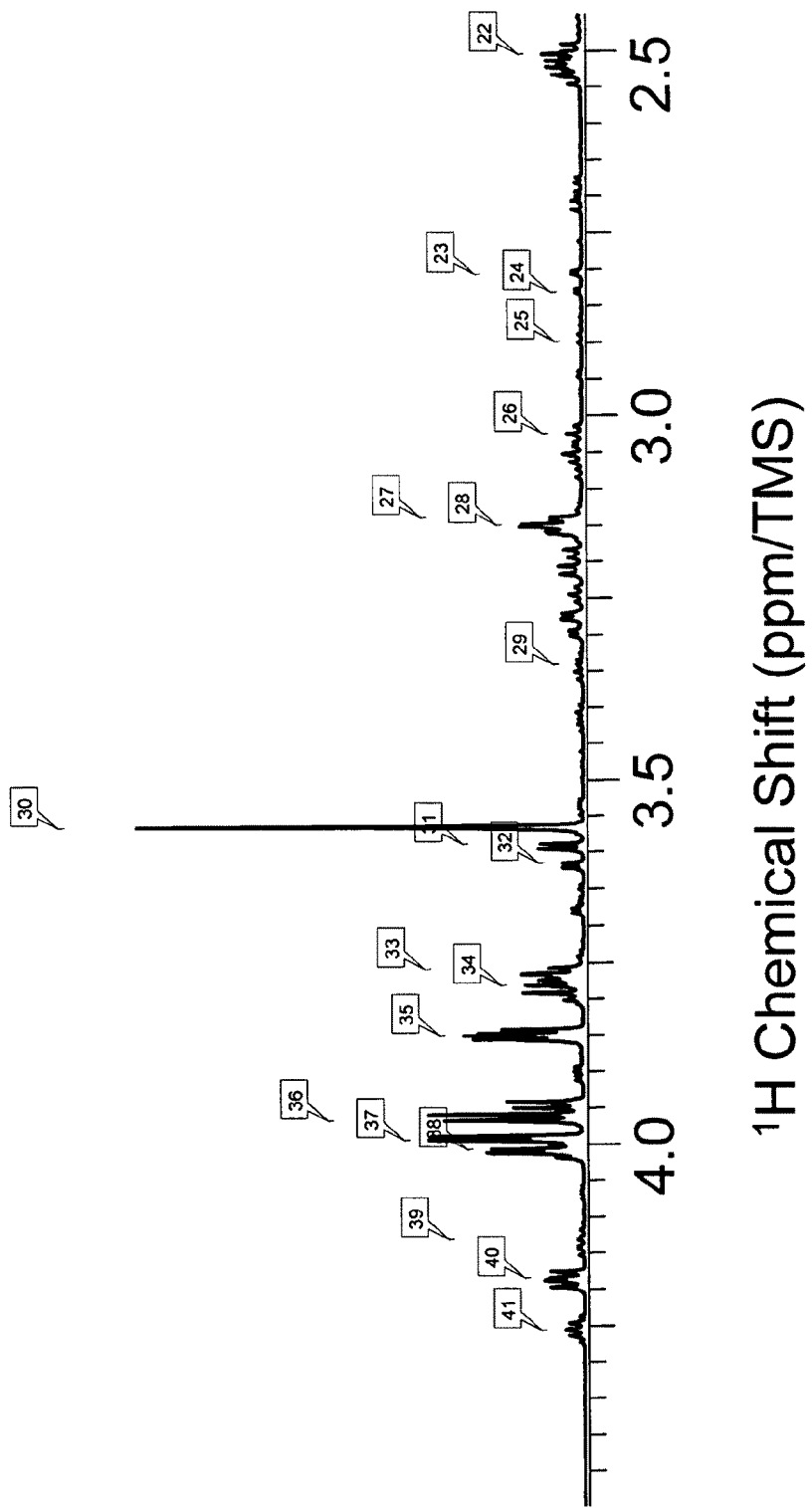
FIG. 1B shows $^1$H NMR spectrum per FIG. 1A showing chemical shift range of about 2.5 to 4.5 ppm.
Figure 1C:
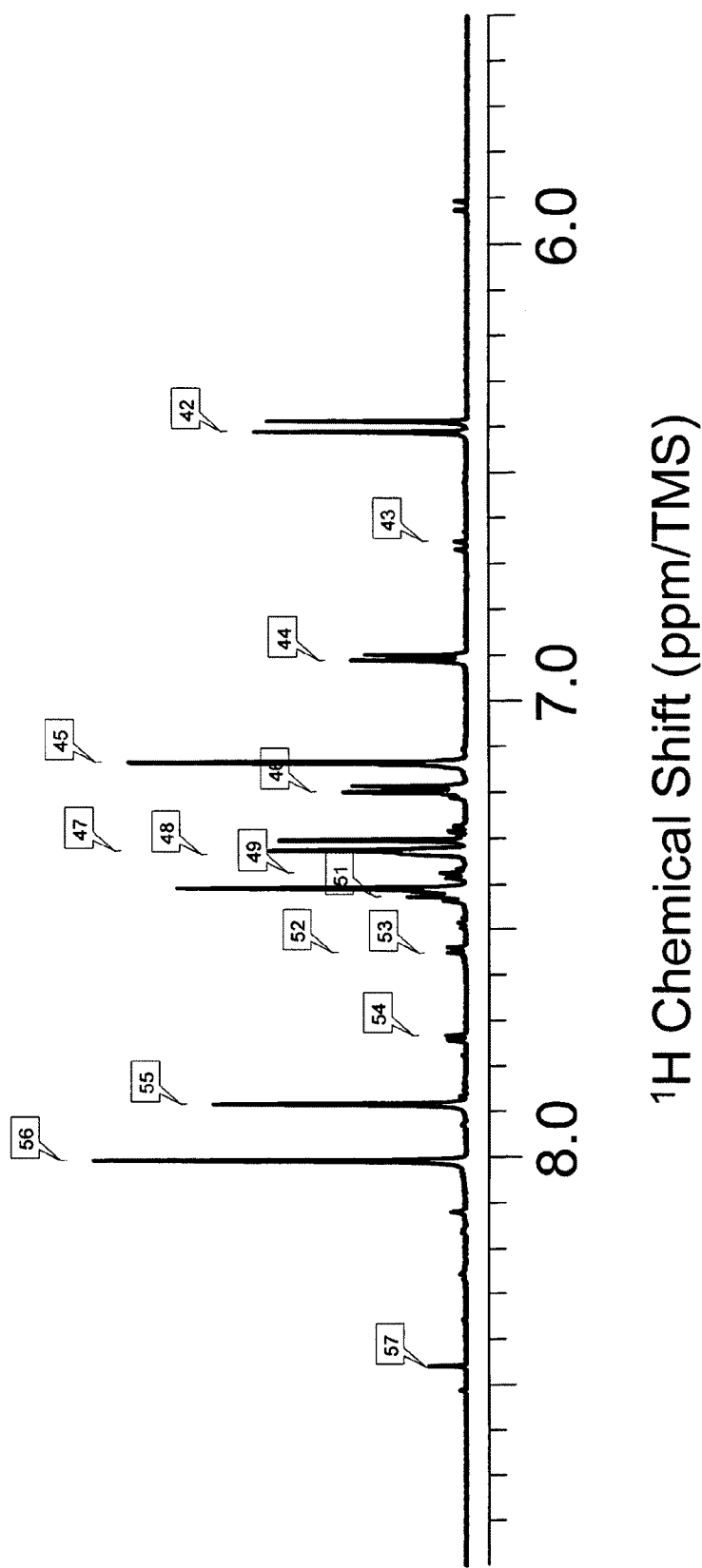
FIG. 1C shows $^1$H NMR spectrum per FIG. 1A showing chemical shift range of about 5.5 to 8.5 ppm.

The 700 MHz $^1$H NMR spectra of an aqueous extraction of a tape strip collected from occluded adult forearm skin are shown in FIG. 1A, FIG. 1B and FIG. 1C along with $^1$H resonance assignments. The assignments are based on a combination of spiking experiments and literature references as noted earlier. They are: 1 alpha-OH-n-butyrate; 2 lipid (—H$_3$); 3 isoleucine; 4 leucine; 5 valine; 6 isoleucine; 7 valine; 8 lactate; 9 alanine; 10 leucine; 11 lysine, 12 lysine; 13 acetate; 14 proline; 15 glycoprotein; 16 proline; 17 glutamine; 18 acetoacetate; 19 valine; 20 glutamate; 21 glutamine; 22 glutamate; 23 N—CH₃; 24 CH3 next to NH; 25 N—CH3; 26 lysine; 27 citrulline; 28 phenylalanine; 29 proline; 30 glycine; 31 threonine; 32 valine; 33 alpha-H from amino acids; 34 alanine; 35 serine; 36 hippurate; 37 histidine; 38 phenylalanine; 39 lactate; 40 beta-OH-butyrate; 41 threonine; 42 urocanate; 43 trans-aconitate; 44 tyrosine; 45 histidine; 46 tyrosine; 47 urocanate; 48 phenylalanine; 49 phenylalanine; 50 urocanate; 51 phenylalanine; 52 hippurate; 53 tryptophan; 54 tryptophan; 55 urocanate; 56 histidine; 57 formate.

Figure 2A:
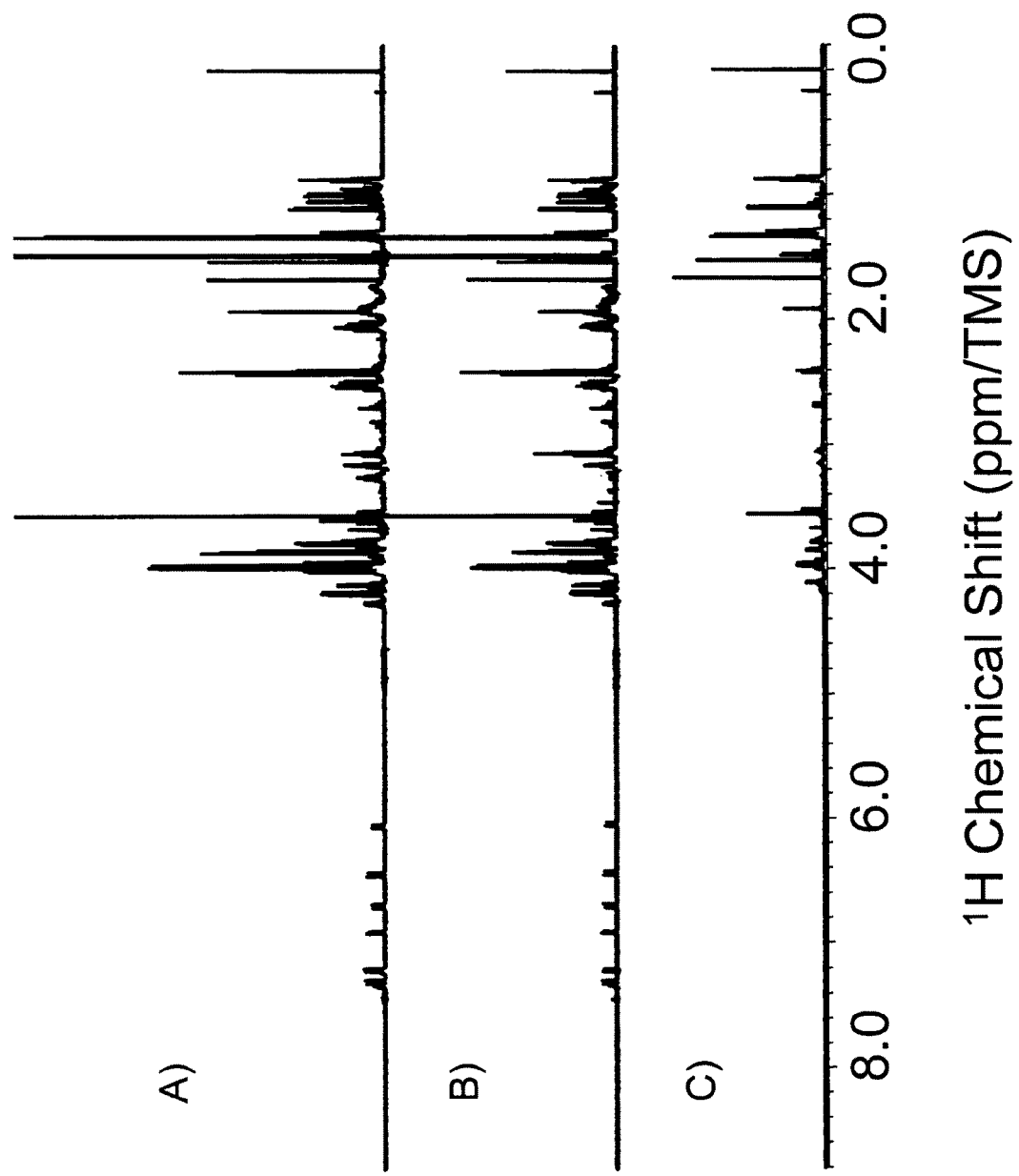
FIG. 2A shows 600 MHz $^1$H NMR spectra of extraction of tape strips collected from adult forearm skin following full occlusion for 72 hours (A), partial occlusion for 72 hours (B), non-occluded control (C). Water resonance (about 4.8 ppm) is excluded.
Figure 2B:
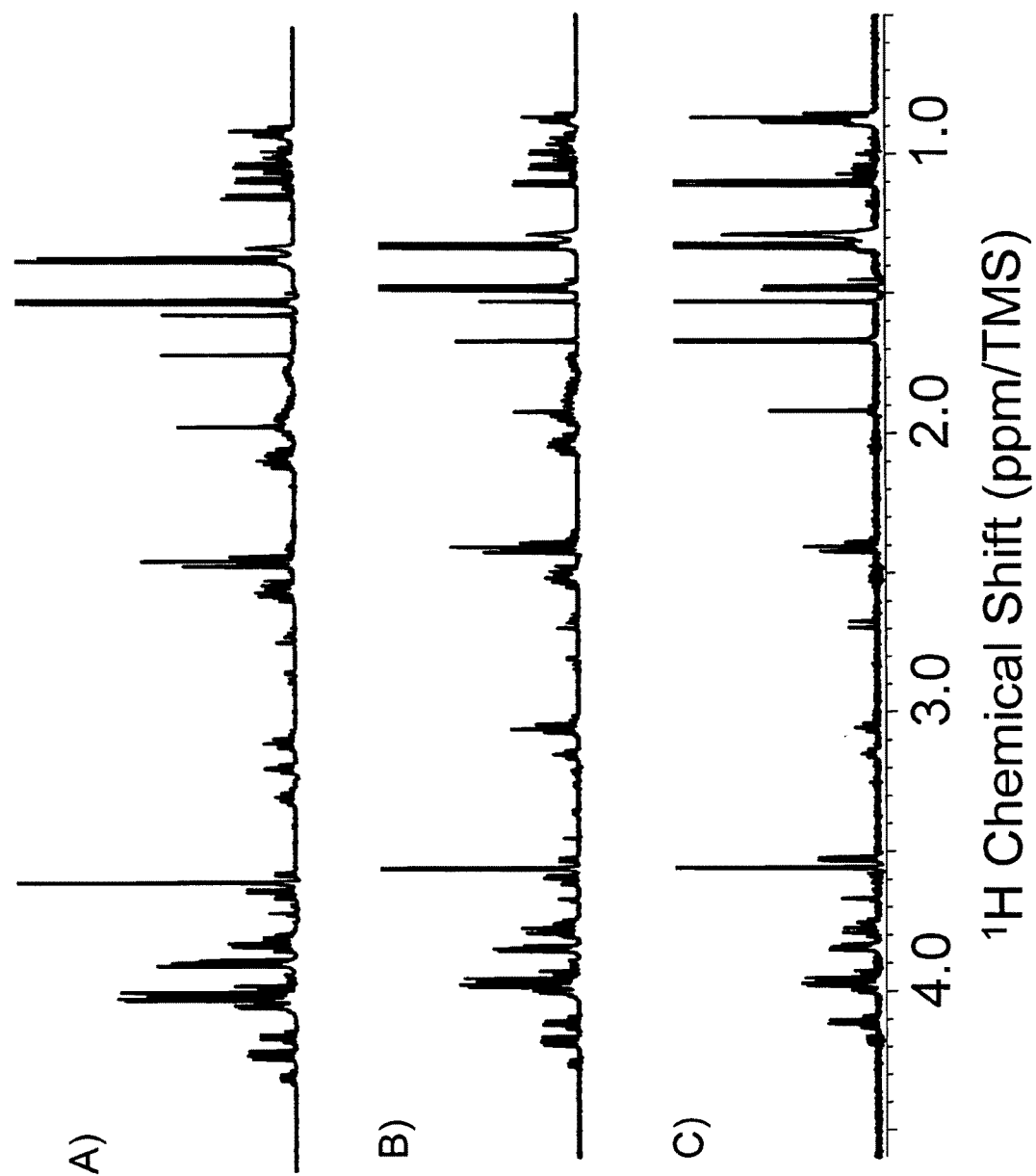
FIG. 2B shows expanded aliphatic regions corresponding to $^1$H NMR spectra in FIG. 2A.
Figure 2C:
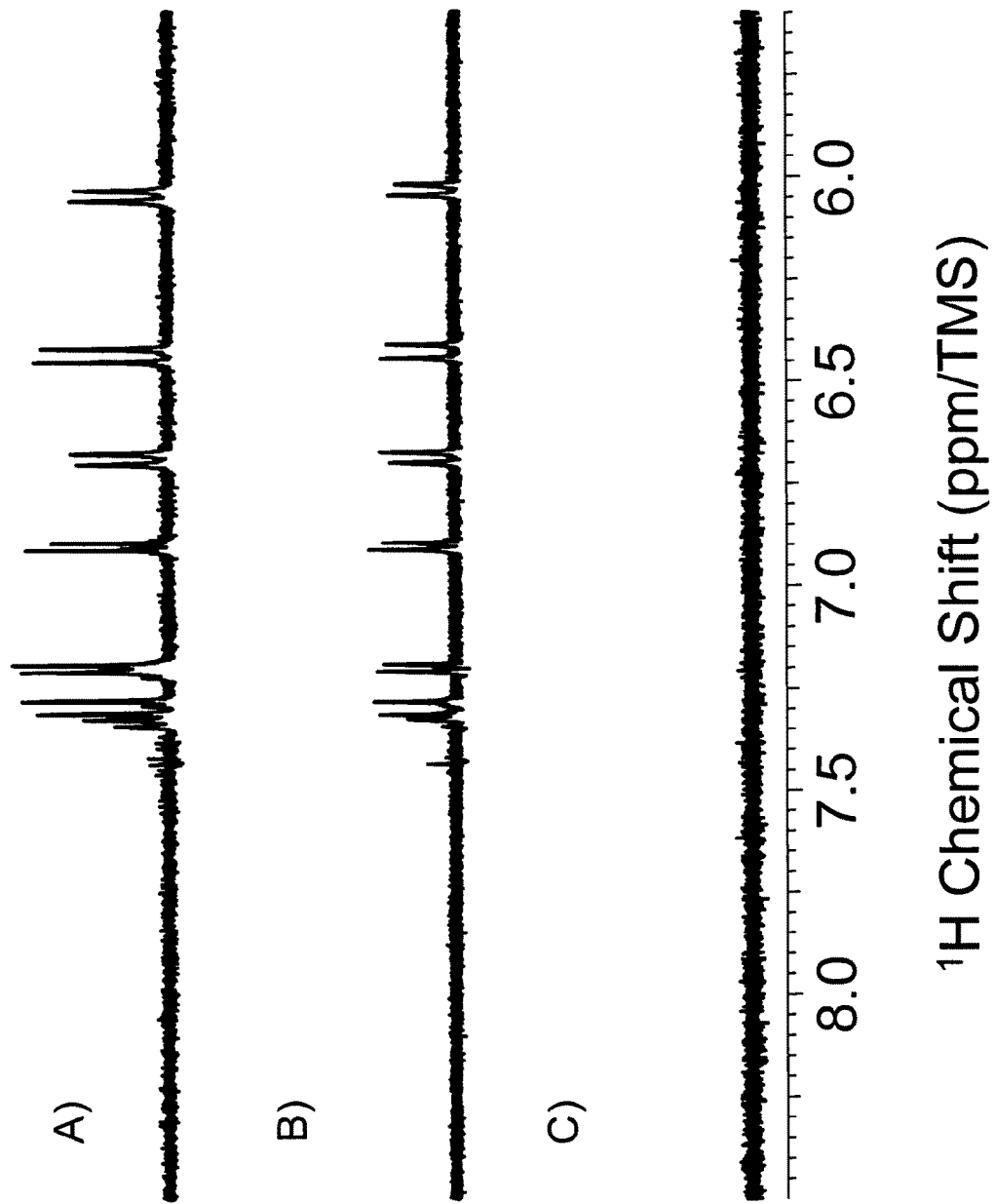
FIG. 2C shows expanded aromatic regions corresponding to $^1$H NMR spectra in FIG. 2A.

FIG. 2A shows the spectra of skin samples taken from a subject after 72 hour occlusion. The spectra are acquired on a Varian INOVA-500. Because of the small sample volume, a 3 mm indirect detection probe is used. FIG. 2B shows the aliphatic regions of the spectra of FIG. 2A. FIG. 2C shows the aromatic regions of the spectra of FIG. 2A. NMR spectra of untreated and occluded with partial breathable (partial occlusion) and non breathable materials (full occlusion) in FIG. 2A, FIG. 2B and FIG. 2C may show the changes both in aliphatic and aromatic region (bottom trace—non-occluded control, the middle trace—partial occluded and upper trace—full occluded). With the occlusion protocol, occlusion induced skin changes are easily detected.

Example 2

Identification of Skin Metabolites

Skin metabolites that respond to occlusion are identified using various approaches. Samples from occluded and control skin are collected following the same method described in Example 1.

The skin strips are extracted with water and then analyzed by capLC-MS/MS (LCQ LC-MS/MS system (ThermoFinnigan) with 173A Microblotter-Capillary LC system (Applied Biosystems) and a 0.5 mm×15 cm C18 capillary column (Perkin Elmer). Comparison of the MS data reveal a unique signal with m/z 139 whose intensity is elevated in occluded skin. Exact mass measurement of the peak indicates a molecular ion of m/z 139.0518 with a possible molecular formula of $C_6H_6N_2O_2$. There are several possible structures with the same molecular formula and similar mass spectra.

Several known compounds are tested having these characteristics using MS/MS, and urocanic acid is identified as the biomarker in the occluded skin. Urocanic acid (UCA) is a natural component in the stratum corneum and is a metabolite formed by one step enzymatic reaction (deamination) from histidine. Trans-UCA is a natural form in stratum corneum. It can be converted to cis-UCA via UV irradiation or sun exposure. In order to confirm the biomarker identity, two separate experiments may be performed using capillary electrophoresis (CE).

First, a pure UCA sample from Sigma is run through CE and a single peak is observed. The same sample solution is then exposed to UV light for one hour and run through CE again. The single UCA peak splits into two peaks. The original UCA peak becomes smaller while a new peak appears with a shorter migration time. The migration time of both trans- and cis-UCA match that of the two peaks of the biomarkers in an occluded skin extract.

Second, a sample from occluded skin is analyzed by CE before and after UV exposure. As expected, the ratio of the biomarker peaks changes after UV exposure. The peak corresponding to trans-UCA becomes smaller while the other peak (cis-form) becomes larger. In a spiking test, the two peaks of UCA isomers superimpose to those of the skin extract. The two peaks found in CE of occluded skin are thus confirmed as cis- and trans-UCA.

Confirmation of the metabolites involved with skin conditions is then assessed, along with the possibility that monitoring levels of metabolites identified could lead to useful models that could predict unknown samples.

Figure 3:
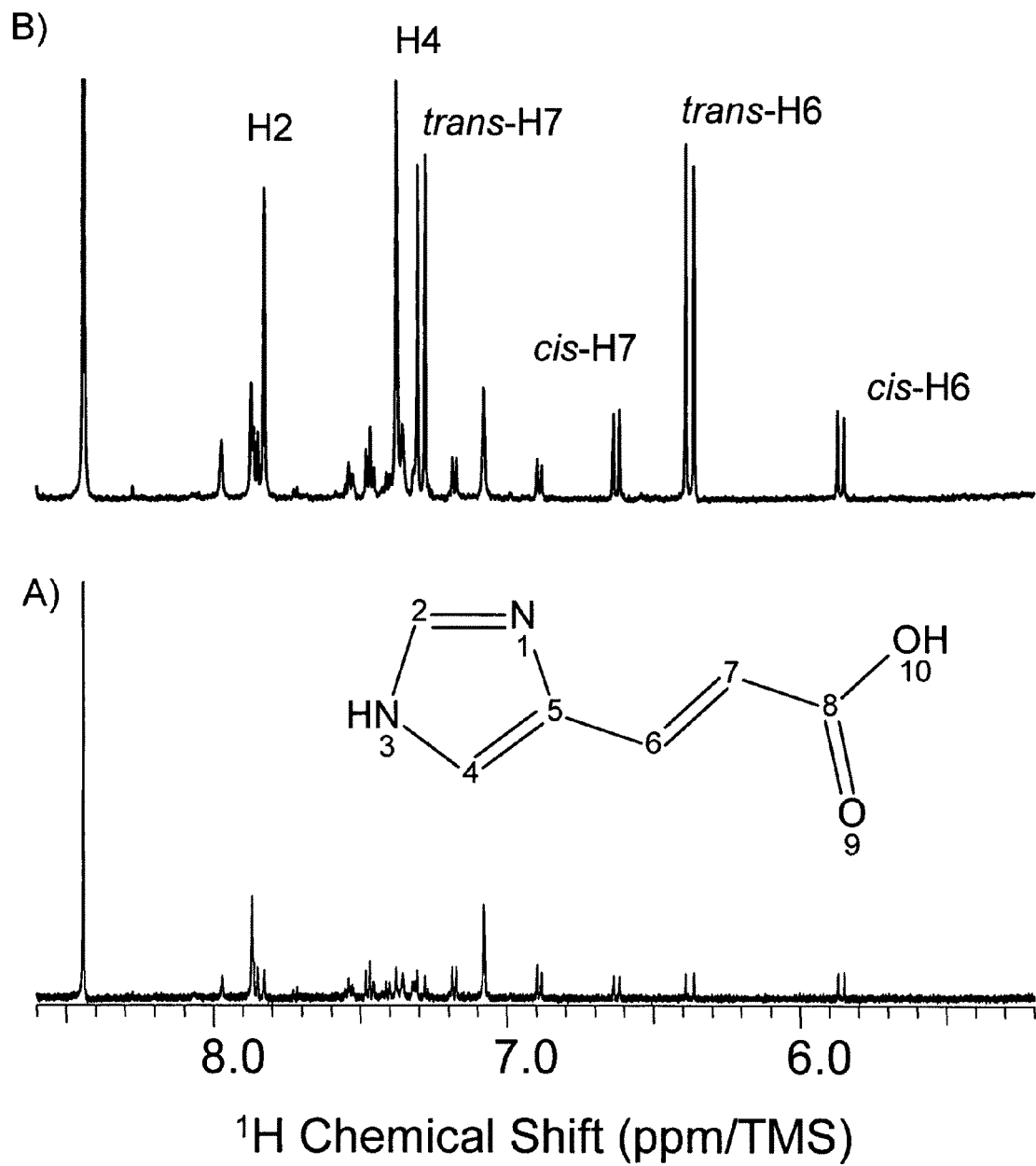
FIG. 3 shows 600 MHz $^1$H NMR spectra (aromatic region) of tape strip extractions of adult forearm skin (A) and with cis- and trans-urocanic acid spike (B). Chemical structure of trans-urocanic acid shown as insert.

A fully occlusive patch (Saran Wrap®) is applied to forearm skin overnight. Skin samples by D-Squame™ tape stripping are taken from both treated and control (non-occluded) sites. The samples are extracted by placing a single skin strip in a glass vial, adding 1 mL water and sonicating the vials for 30 min. The sample extracts are dried under nitrogen ($N_2$) and are reconstituted in 200 µL of 200 mM sodium phosphate containing 0.1% (w/v) sodium azide in $D_2O$ at pH 7.4. The samples are transferred to sample tubes for $^1H$ NMR analysis. A 2.5 mm probe is used due to the small sample size. The $^1H$ NMR spectra are collected using a 600 MHz Bruker Avance NMR spectrometer employing a routine preset pulse sequence. A known amount of UCA solution is spiked into the skin extract and analyzed via $^1H$ NMR again. The NMR spectra may show enhanced peaks corresponding to the spiked UCA and facilitate the identification of the compound that varies as a function of occlusion (FIG. 3).

Figure 4A:
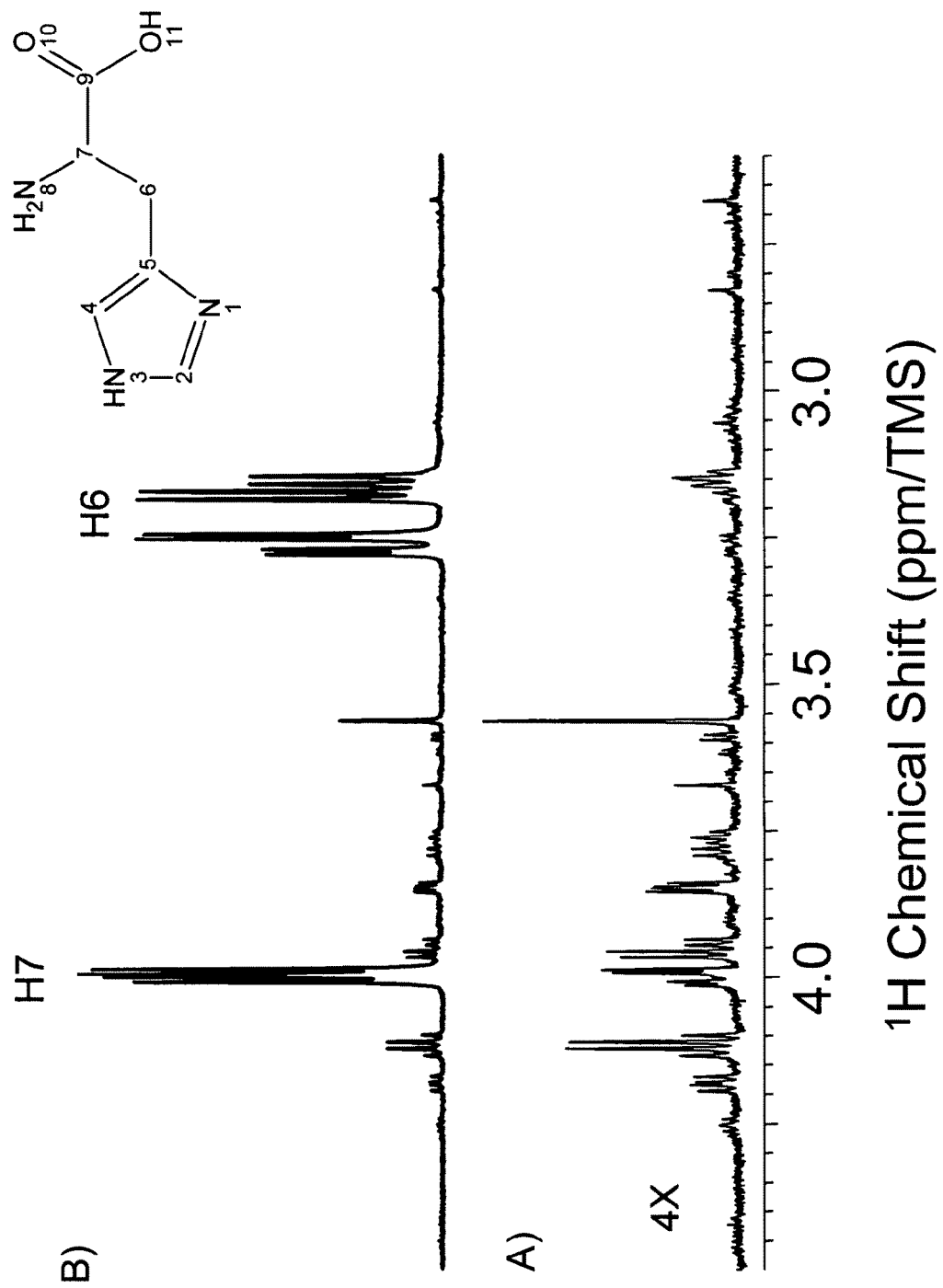
FIG. 4A shows 600 MHz $^1$H NMR spectra (aliphatic region) of tape strip extractions of adult forearm skin (A) and with histidine spike (B). Chemical structure of histidine shown as insert.
Figure 4B:
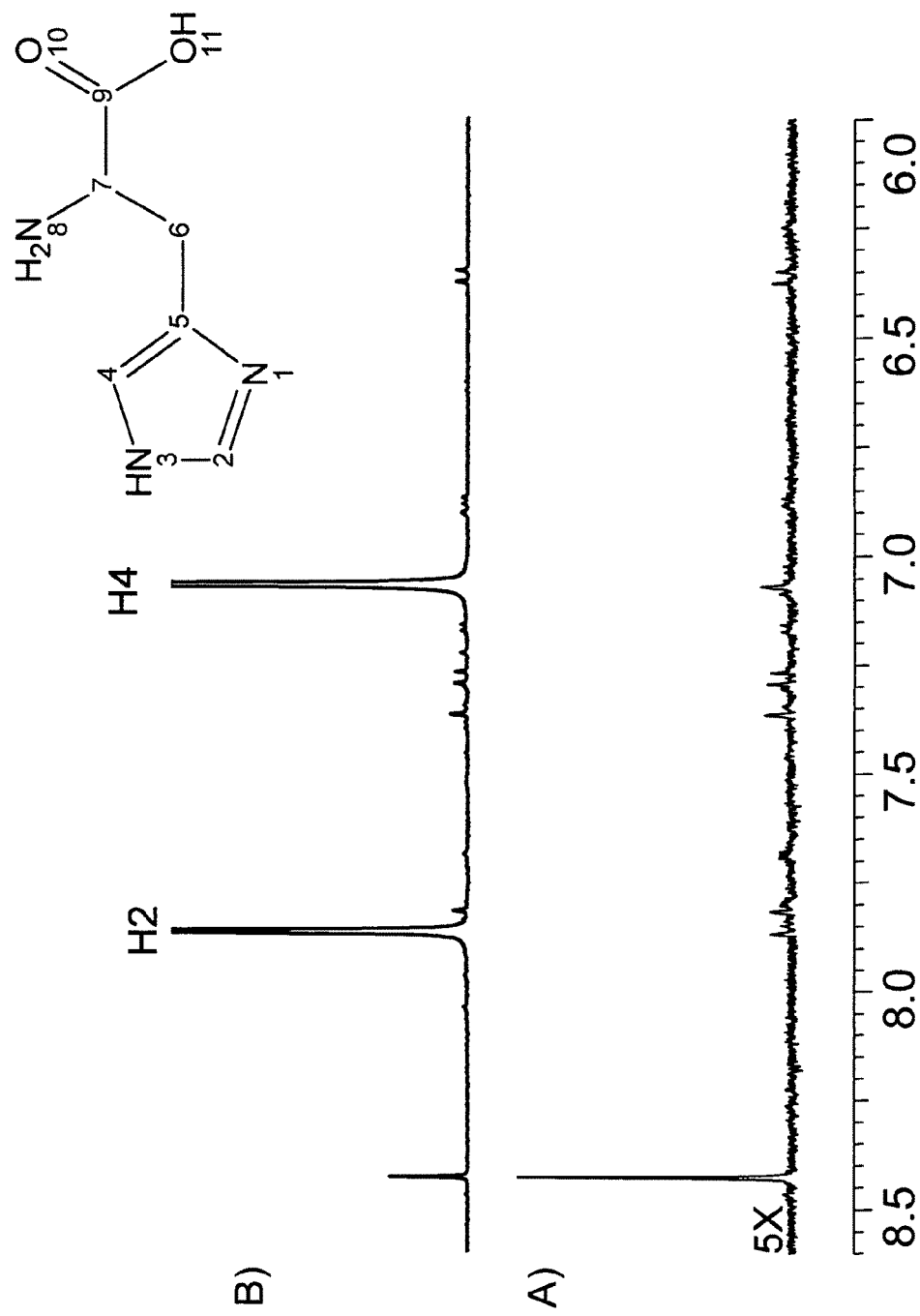
FIG. 4B shows 600 MHz $^1$H NMR spectra (aromatic region) of tape strip extractions of adult forearm skin (A) and with histidine spike (B). Chemical structure of histidine shown as insert.
Figure 5:
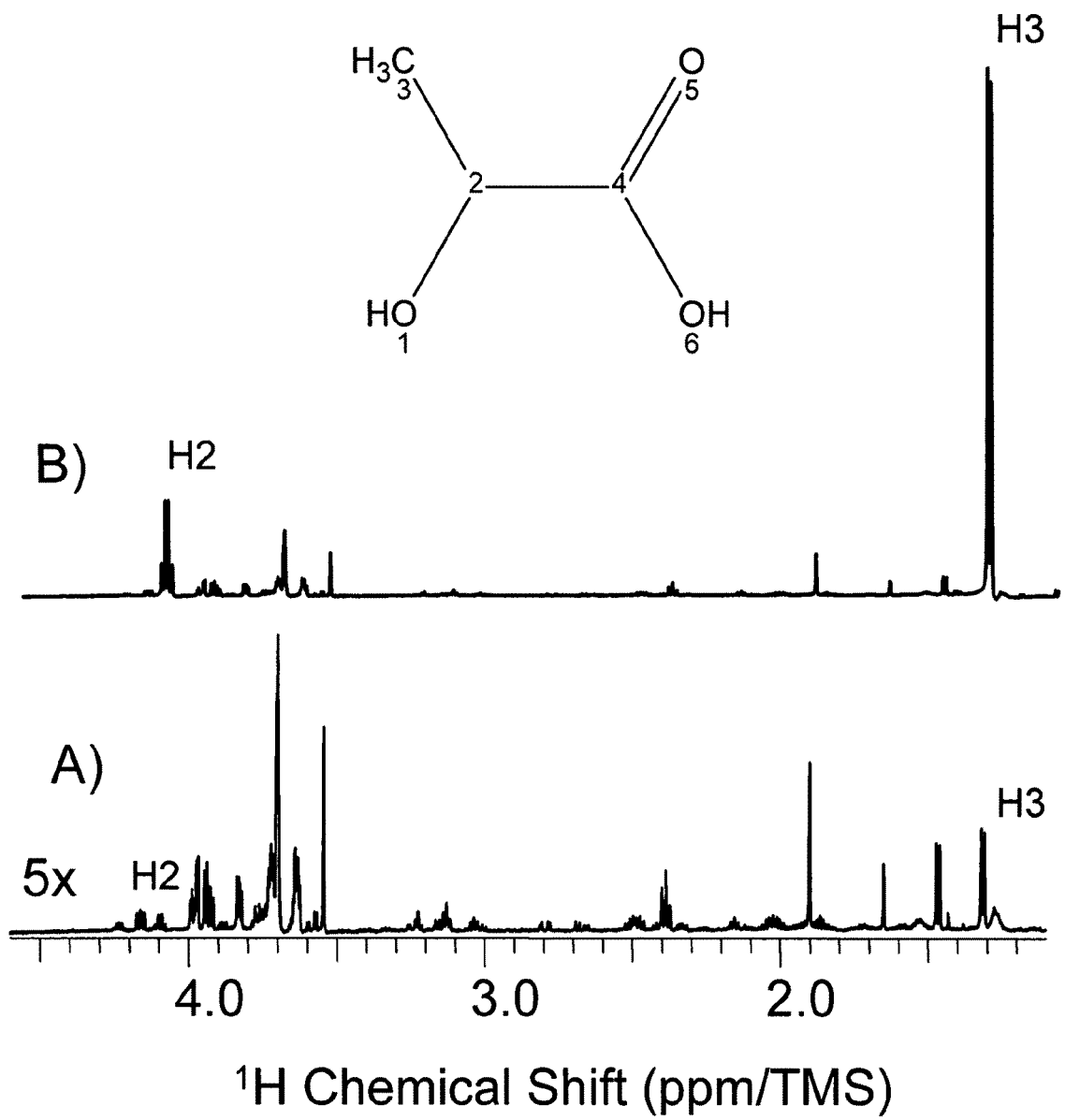
FIG. 5 shows 600 MHz $^1$H NMR spectra (aliphatic region) of tape strip extractions of adult forearm skin (A) and with lactic acid spike (B). Chemical structure of lactic acid shown as insert.

In addition to identification of cis-urocanic acid (cis-UCA) and trans-urocanic acid (trans-UCA) (FIG. 3), histidine (FIG. 4A and FIG. 4B), and lactate (FIG. 5) are also identified using the above approach.

Example 3

Sample Variation Effects on Metabolite Profiles

Metabolite variations among skin type, depth, site, and time from washing are assessed. Five different sites from an adult forearm are stripped once using D-Squame™ tapes one hour after washing. The same five sites are stripped again six hours after the first tape stripping. An additional set of samples are tape stripped consecutively ten times from a separate site for skin depth profile study. Skin depth samples are also collected from another individual. The samples are extracted by placing a single skin strip in a glass vial, adding 1 mL water and sonicating the vial for 30 min. The sample extracts are dried under nitrogen ($N_2$) and are reconstituted in 200 µL of 200 mM sodium phosphate containing 0.1% (w/v) sodium azide in $D_2O$ at pH 7.4, and transferred to a 2 mm capillary tube capped with a Teflon™ fixture. The capillary tube is inserted into a NMR micro sample tube assembly (5 mm tube with 3 mm stem, from NewEra (New Jersey)). Annular space is filled with $D_2O$ to provide locking during spectrometer setup for $^1H$ NMR. Metabolite profiles of the ten consecutive tape strips from a single site are compared.

Results may suggest that within the same individual, there is no significant chemical compositional difference up to ten tape strips in depth. However, the level of the water-extractable metabolite components may be gradually reduced as the tape stripping progresses in depth. Samples from individuals in this study may show similar gradient distribution. To mitigate the variation, the optimal depth of skin sampling should be determined and used for sample to sample comparison.

Within the same individual, different sites on the forearm may not show significant differences in the metabolic composition when freshly cleaned up to one hour after shower. However, variation may become observable over time after the first tape stripping, which may be a result of physical activity and clothing, such as a site having the most significant change may be close to the wrist. Control of skin environment may reduce the variation.

For example, the level of water-extractable metabolites may be higher in skin strips taken at six hours post washing than the first strips taken at one hour post washing. The increased level of metabolites in the six hour strips may be observed in all five sites. This increase may be due to a skin response to disrupted barrier by the first stripping or as a result of natural accumulation of the metabolites in the skin during the day. There is no significant chemical composition change among the strips taken from two different times.

Visual inspection of the spectra suggests that there is some difference in the profile of skin metabolites between the individuals in this study. Such differences are not surprising given the inherent differences in metabolic activity, physical activity, and life style. In this specific study, lactic acid levels are found to vary between individuals.

Example 4

Measuring Metabolites of Samples to Assess State of Skin

Skin metabonomics is able to discriminate metabolite profile variation and is very useful for evaluating skin biochemical states, optimizing clinical study design and interpreting clinical results. There are many factors responsible for skin changes. Factors such as bowel movement (BM), urine, pH and temperature are among these factors and may impact skin simultaneously in a diapered environment. Typical examples are leg crease areas that are typically occluded while lower buttock areas experience more insults from repeated BM and urine soiling and frequent over-hydration. NMR is able to detect the combined impact of these factors on skin and differentiate these skin states. Skin treatment efficacy such as wipe cleaning can also be evaluated and documented by NMR analysis.

The predictive aspect of the models of the above testing samples may be examined in the following experiment.

Figure 6:
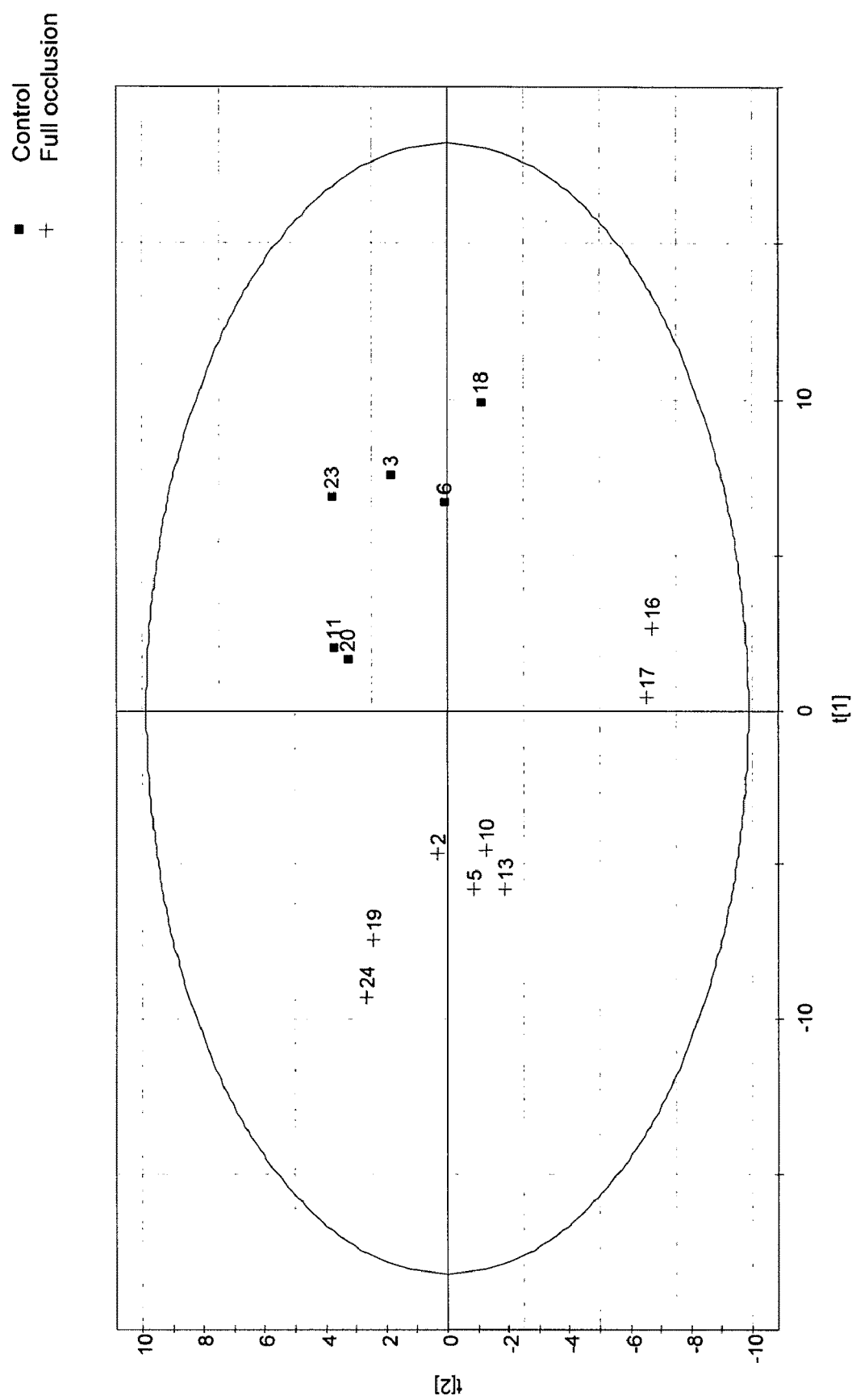
FIG. 6 shows a scores plot for skin samples grouped into occluded and control.

The NMR data from skin samples, such as those from Example 1, may be processed using Partial Least Squares-Discriminant Analysis (PLS-DA) (SIMCA-P+ from Umetrics) and the scores plot is shown in FIG. 6. The skin sample numbers shown in FIG. 6 may be identified as follows in Table 1.

TABLE 1

| Skin Sample Number | Skin Sample Code |
|---|---|
| 2 | 24 hr full occlusion (2__24__f) |
| 3 | 24 hr full occlusion (3__24__t) |
| 5 | 72 hr full occlusion (5__72__f) |
| 6 | Control (6__72__c) |
| 10 | 72 hr full occlusion (10__72__f) |
| 11 | Control (11__72__c) |
| 13 | 24 hr full occlusion (13__24__f) |
| 16 | 72 hr full occlusion (16__72__f) |
| 17 | 72 hr full occlusion (17__72__f) |
| 18 | Control (18__72__c) |
| 19 | 72 hr full occlusion (19__72__f) |
| 20 | Control (20__72__c) |
| 23 | Control (23__72__c) |
| 24 | 72 hr full occlusion (24__72__f) |

Referring to FIG. 6, the occluded skin samples and those from the non-occluded skin are separated into disparate groups. Some of the metabolites are highly elevated, such as UCA, in occluded skin. The extent of occlusion can be assessed based on the level of similarity to untreated (Class 1) or full occluded skin (Class 2) as predicted by PLS-DA calculation. The training set used to generate FIG. 6, may define a model to predict skin classification of partially occluded skin samples.

Partial occlusions may be a useful model for that of diapered skin and could be responsible for inducing skin irritation like that in leg creases or may not cause any visible redness as in upper buttock area. The skin responses can be a Class 1-like the control, Class 2-like full occlusion, or something in between. The values in Table 2 (in sample ID: f-full occlusion, p-partial occlusion and c-control) may demonstrate a possibility of predicting the extent of partial occlusion on diapered and other types of skin environments. The prediction is demonstrated in Table 2 below. "Similarity to Control" score close to 1 in the analysis is classified as control (Class 1) and "Similarity to Full Occlusion" score close to 1 in the analysis is classified as full occlusion (Class 2). Almost all of the full occlusion and control skin can be predicted correctly by the prediction calculation. The similarity value of the treated skin to Class 1 or Class 2 offers a measure to rank order skin for its response to the treatment or product use.

TABLE 2

| Sample Code | Subject | Treatment | PLS-DA Class | Similarity to Control | Similarity to Full Occlusion |
|---|---|---|---|---|---|
| 1__24__p | A | 24 hr partial occl. | | 0.82413 | 0.17586 |
| 2__24__f | | 24 hr full occl. | 2 | 0.04026 | 0.95973 |
| 3__24__c | | 24 hr control | 1 | 1.00391 | −0.0039 |
| 10__72__f | B | 72 hr full occl. | 2 | 0.0733 | 0.92669 |
| 11__72__c | | 72 hr control | 1 | 0.97606 | 0.02393 |
| 12__72-p | | 72 hr partial occl. | | 0.6589 | 0.34109 |
| 19__72__f | C | 72 hr full occl | 2 | −0.029 | 1.02908 |
| 20__72__c | | 72 hr control | 1 | 0.96491 | 0.03508 |
| 21__72__p | | 72 hr partial occl. | | 0.19195 | 0.80804 |

Example 5

Metabolites at Various Skin Sites

Baby skin in a diaper environment may be slightly different due to its local environment. For example, skin in leg creases is typically occluded whereas that in the lower buttock area is over-hydrated and experiences more abrasions. Metabonomics has the power to distinguish the differences.

Figure 7A:
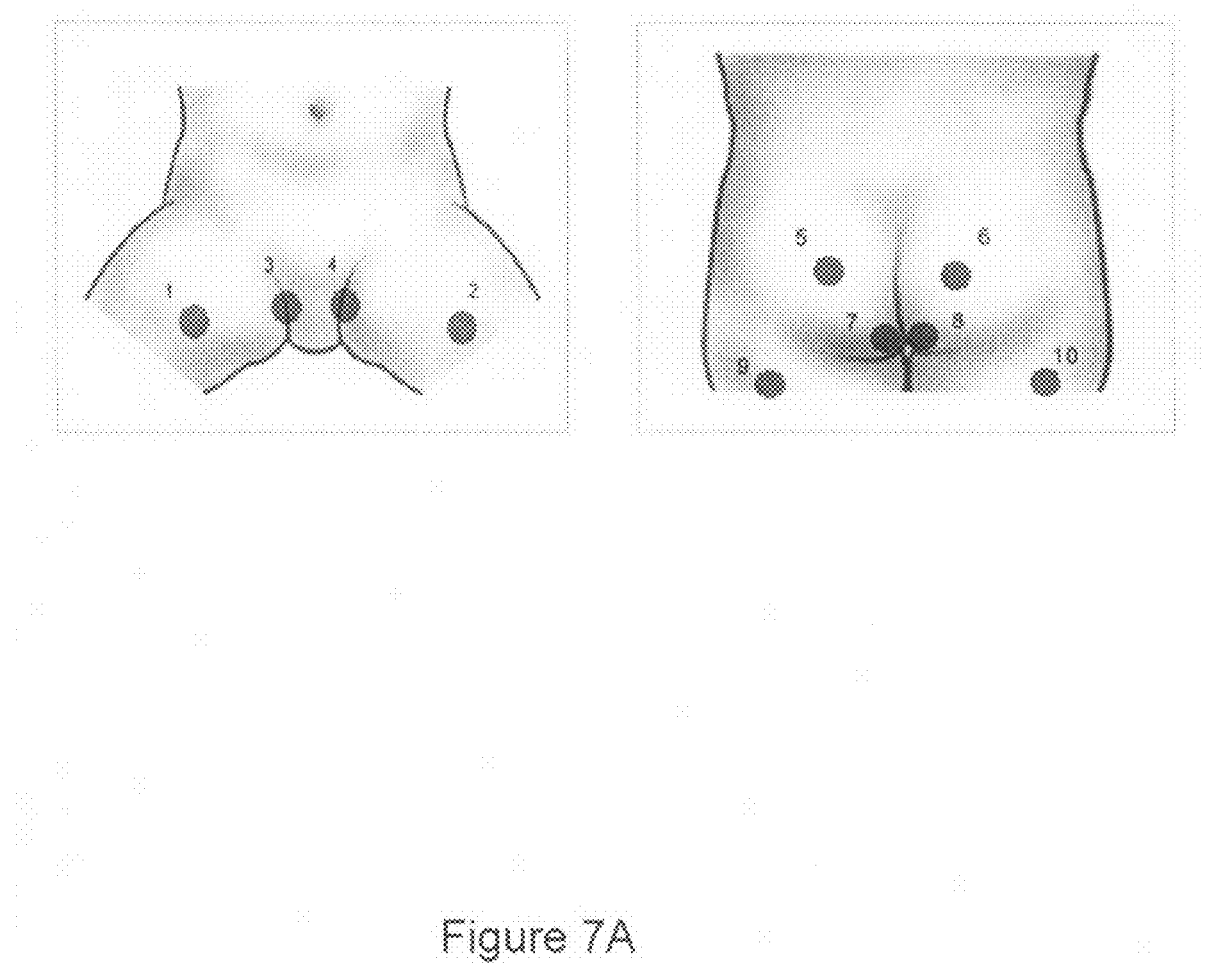
FIG. 7A shows a diagram identifying various test sites of baby skin.

Ten skin samples from both opposite sites of a baby's behind (left vs. right side) are collected, two from each type of skin site (FIG. 7A): intertriginous region (leg crease area)(3 & 4 in FIG. 7A), front thigh (1 & 2 in FIG. 7A), lower buttock (7 & 8 in FIG. 7A), upper buttock (5 & 6 in FIG. 7A), and back thigh (9 & 10 in FIG. 7A). The samples are prepared as follows. The samples are extracted by placing a single skin strip in a glass vial, adding 1 mL water and sonicating the vial for 30 min. The sample extracts from both opposite sites are combined and are dried under nitrogen ($N_2$) and are reconstituted in 200 μL of 200 mM sodium phosphate containing 0.1% (w/v) sodium azide in $D_2O$ at pH 7.4. The samples are transferred to sample tubes for $^1H$ NMR analysis. The $^1H$ NMR data are collected on a Bruker Avance 600 MHz instrument running XWINNMR (as available in the Bruker Avance software system) and equipped with a 2.5 mm Broad Band Inverse (BBI) probe. A presat pulse program is used for water suppression. A total number of 2048 scans are collected.

Figure 7B:
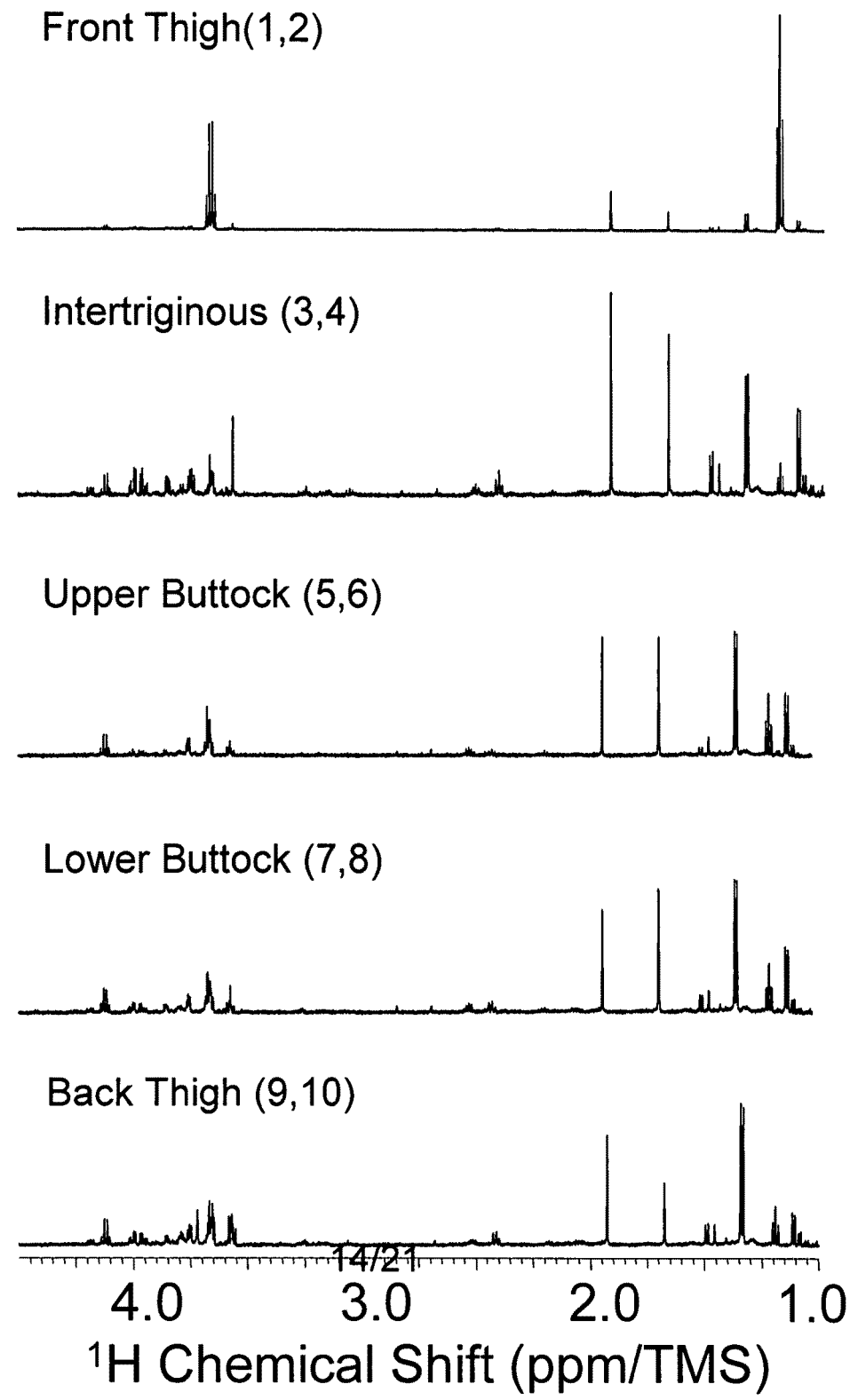
FIG. 7B shows 600 MHz $^1$H NMR spectra (aliphatic region) of aqueous extractions of tape strips from the various sites as identified in FIG. 7A.
Figure 7C:
FIG. 7C shows 600 MHz $^1$H NMR spectra (aromatic region) of aqueous extractions of tape strips from the various sites as identified in FIG. 7A.
Figure 7C:
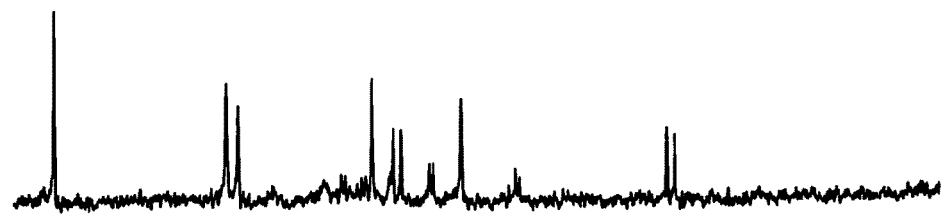
Figure 7C:
Figure 7C:
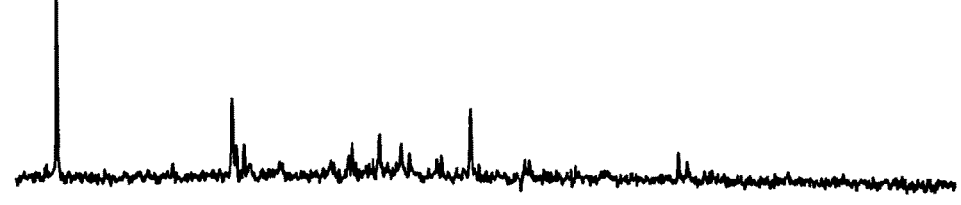
Figure 7C:
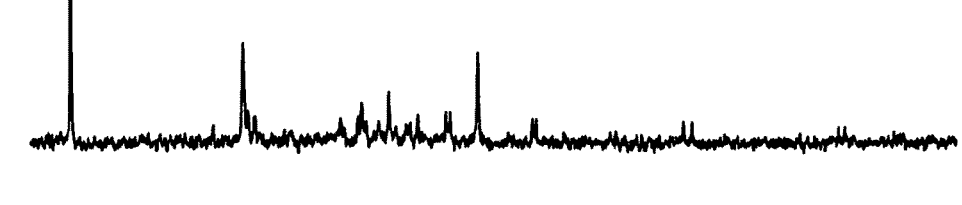

The proton resonances from these samples are similar in the aliphatic region (FIG. 7B). However, in the aromatic region (FIG. 7C), UCA signals are stronger in skin samples from intertriginous regions than those from the back thigh. The UCA resonances from other sites are weaker (6.4, 7.37, 7.41 and 7.88 ppm).

This result may be consistent with previous skin studies wherein levels of UCA increased upon skin occlusion. The intertriginous (leg crease) area is constantly under abrasive and non-breathable conditions, therefore the region is more occluded than other areas. Lack of UCA signal from the lower buttock region could be due to the overhydration and rewetting during diaper wearing. Skin chafing might be the major cause of the elevated UCA levels in the back thighs. Lack of cis-UCA signals in the baby leg crease skin sample may be explained as lack of sun light exposure, and therefore, no photochemical isomerization from trans-UCA to cis-UCA.

Example 6

Measuring Occlusion and Wipes Cleaning Effects

The effects of various skin treatments are assessed by measuring the metabolites from a series of subjects. A set of skin samples from five individuals are analyzed wherein each individual receives six different treatments: Dry control (no treatment); Dry 1 swipe (wipe one time on non-treated skin); Dry 5 swipes (wipe five times on non-treated skin); Wet control (occlusion); Wet 1 swipe (wipe one time on occluded skin); Wet 5 swipes (wipe five times on occluded skin). Tape stripping to collect the skin sample is performed after each treatment. The samples are extracted by placing a single skin strip in a glass vial, adding 1 mL water and sonicating the vial for 30 min and vortexing the samples for 30 seconds. The sample extracts are dried under nitrogen ($N_2$) and are reconstituted in 200 µL of 200 mM sodium phosphate containing 0.1% (w/v) sodium azide in $D_2O$ at pH 7.4. TSP (3-trimethylsilyl-1-propane sulfonic acid sodium salt) may be added. The samples are transferred to 3 mm sample tubes for $^1H$ NMR analysis.

Each sample is manually tuned and shimmed. A preset pulse sequence is used to suppress water signal. Key parameters include nt=2048; at=3.277 s; delay=1.5 s; mixing time=0.1 s; and temp=25° C. A total of 30 spectra are used to generate original data matrix. The data matrix is then analyzed using nmrPro in MATLAB (by Mathworks) environment. The data matrix is pretreated to remove solvent and internal reference peaks, all integrals are scaled to constant value for fair comparison, and noise baseline is cut off by setting appropriate threshold. The preprocessing ensures that factors generated from Molecular Factor Analysis (MFA) (Eads, C., *Analytical Chem.* 76(7):1982-1990 (2004)) are only subject to statistically significant variations. Molecular factor analysis is performed to extract intrinsic grouping potential of the treatments and chemical information about the marker molecules.

Figure 8:
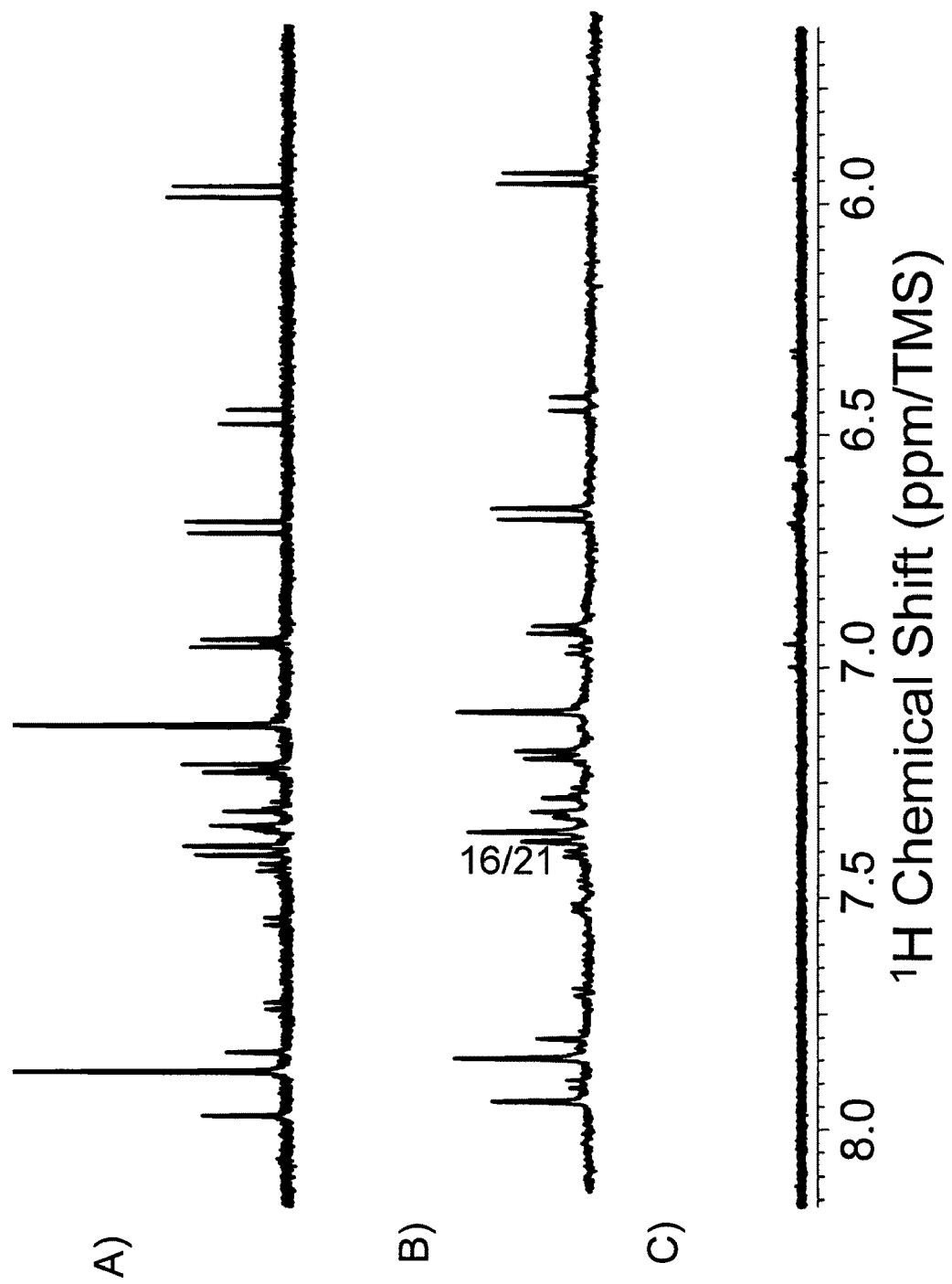
FIG. 8 shows 500 MHz $^1$H NMR spectra (aromatic region) of tape skin extractions of adult forearm occluded skin (A), after one wipe with a ZnO lotion wipe (B), and after five wipes with ZnO lotion wipe (C).

The NMR spectra between individuals may vary, which is not unexpected considering that skin extracts would be expected to differ depending upon each individual's skin type and environment. Upon occlusion (24 hrs, wet treatment), aromatic signals in proton NMR spectrum may increase. The signal intensity may change suggesting metabolic variation during occlusion. The effect that wiping has on skin samples collected is that the amount of extracts found in the skin sample may decrease significantly, for each individual. This result may indicate that wiping removes metabolites from the skin surface and brings skin back to a fresh state. FIG. 8 shows an illustration of, from top to bottom, the NMR spectra from a single subject with occluded skin, occluded skin after one swipe with a zinc oxide (ZnO) wipe (1% ZnO in aqueous solution containing 2% parabens preservative system), and occluded skin after 5 swipes with a ZnO wipe. The spectrum of the skin wiped five times (bottom trace) shows almost no extractable metabolites, indicating that the five wipes removed most if not all metabolites from occluded skin.

Figure 10:
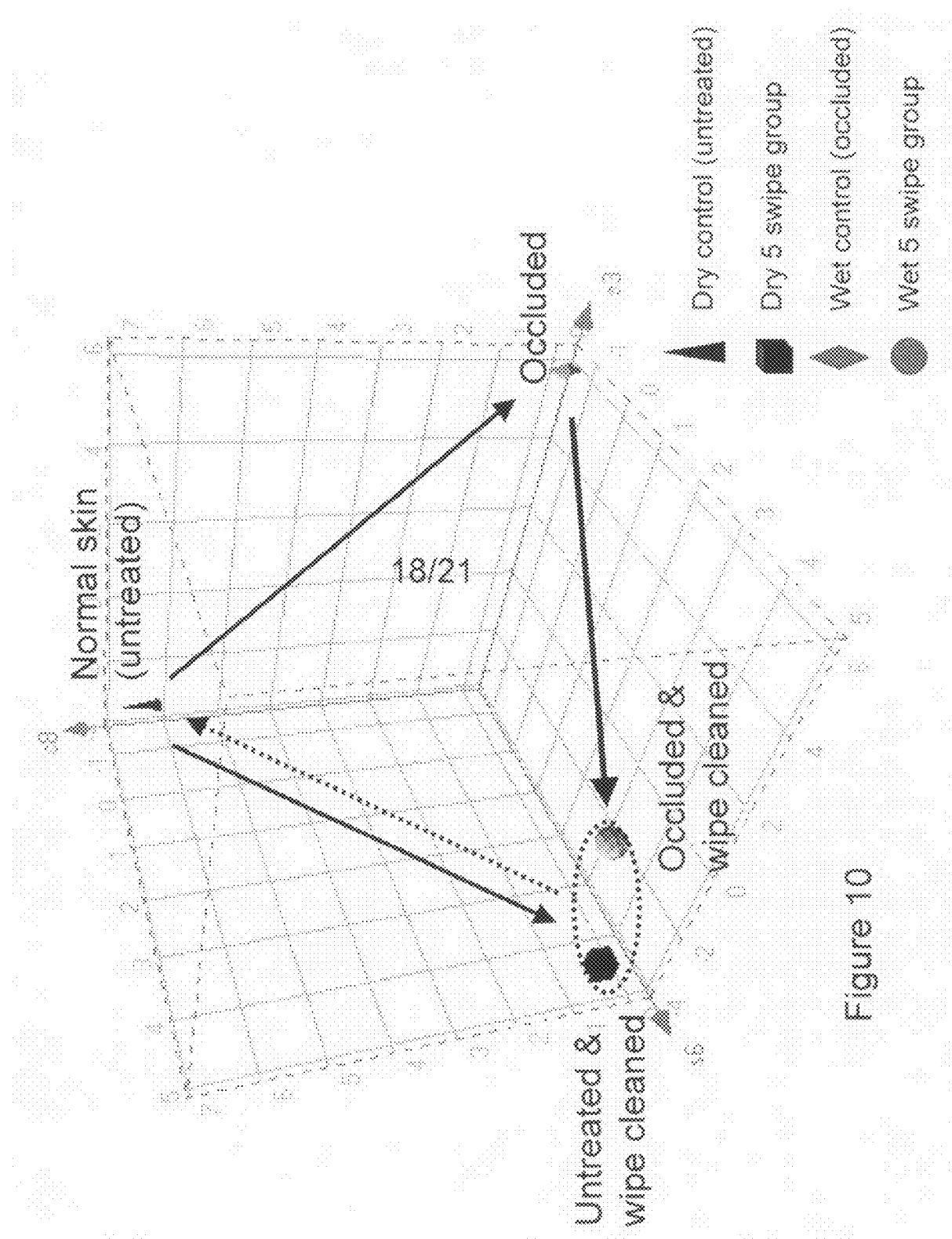
FIG. 10 shows a spatial separation of three skin conditions (untreated normal, occluded, and wipe-cleaned) on a three-dimensional scores plot from a subject.

The NMR data is then processed using MFA and a scores plot on three factors is generated (FIG. 9). The plot shows population separation of dry skin samples from wet skin samples. The Dry control group is clustered away from wet control group. After five wipes, Dry 5 swipe and Wet 5 swipe groups shift to the left of the map, and become more scattered. This is more clearly demonstrated in FIG. 10 for the skin samples from one subject where occlusion may shift skin to a higher score on Factor 3 while wipe cleaning may shift skin to a higher score on Factor 6. The impact of wiping treatment on the skin may be similar regardless of skin pre-treatment (i.e., dry vs. wet). Each factor generated from data analysis may represent either a single metabolite or a combination of multiple marker molecules. The fact that the three factors from MFA may permit differentiation of the untreated (dry) skin from the occluded (wet) skin may indicate metabolic activity differences among skin samples under different treatments.

Occlusion may shift biomarker presentation away from the control biomarker expression pattern. Wiping with lotioned wipes may remove much of the skin metabolites and put both control and occluded skin in a similar normal condition.

Example 7

Assessment and Comparison of Various Treatments

Wiping skin with lotion wipes removes soils from skin surface, leaving skin clean and fresh. A study, in which skin is repeatedly occluded and subsequently wiped cleaned for three days, shows a clear separation of this lotion wipes treated skin from a water and preservative vehicle.

The efficacy of several skin treatments are assessed among a variety of subjects. Samples from 14 subjects are collected. Briefly, the forearm of each subject is occluded for 1 day and then receives one of the 6 treatments listed below. The occlusion is done according to the method as described above. After treatment, the site is occluded again with a fresh occlusion patch. The occlusion/wipe treatment is repeated for a total of 3 days. On the 4th day each site is tape stripped. A total of 84 samples are analyzed—six from each subject in the following categories: occluded control (A); 1.0% ZnO wipe (B); 1.0% ZnO lotion (5 µL/cm$^2$) (C); 1.0% ZnO lotion (1 µL/cm$^2$) (D); water with preservative wipe (E); water with preservative expressed from wipes (5 µL/cm$^2$) (F). Each sample is analyzed using presat pulse sequence for water suppression. The spectra are then transformed into ASCII format and processed using MFA.

Figure 11:
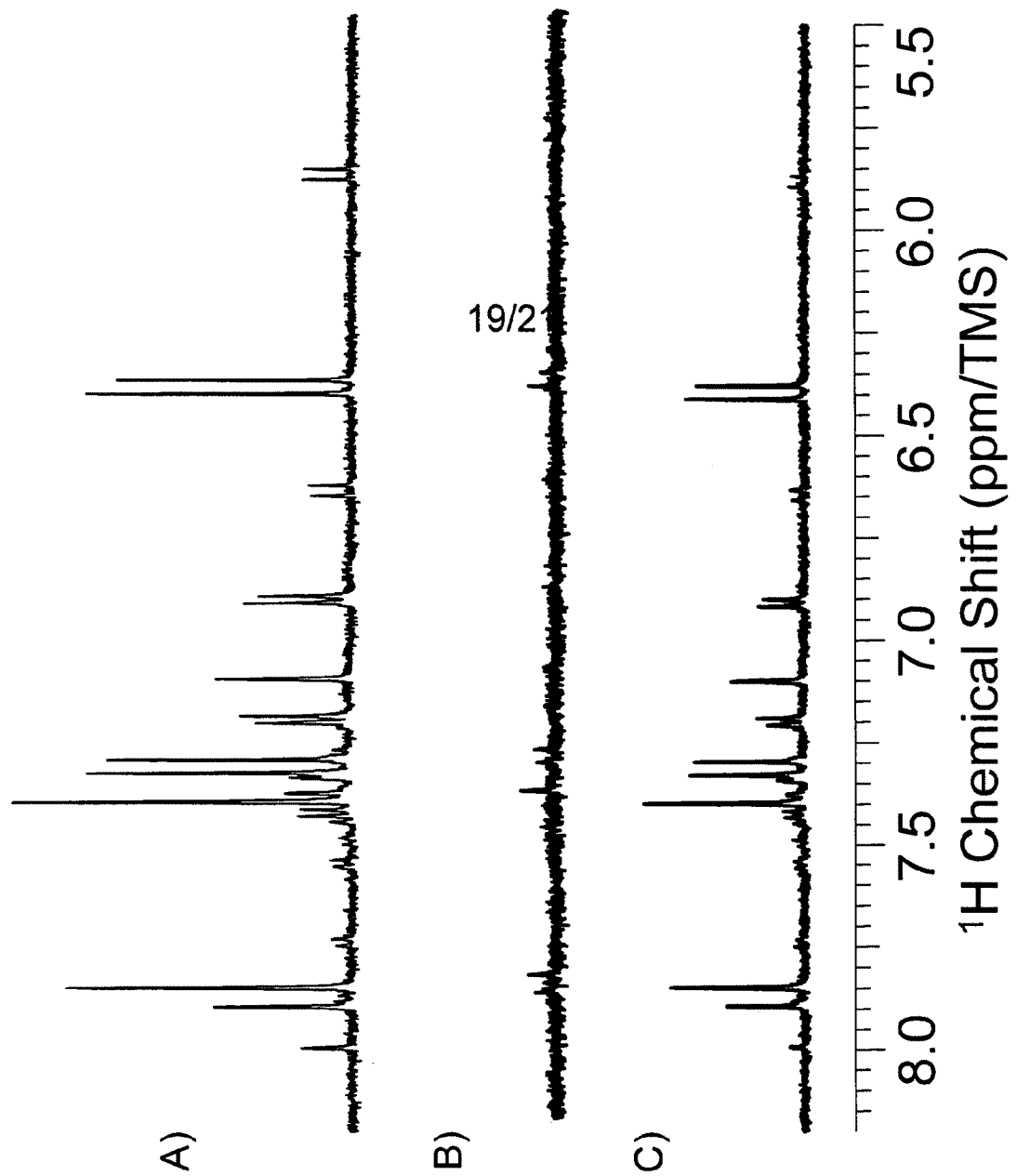
FIG. 11 shows 500 MHz $^1$H NMR spectra (aromatic region) of tape skin extractions of adult forearm occluded skin (A), skin wiped with ZnO lotion wipe (B), and skin wiped with vehicle (water/preservative only) lotion wipe (C).

$^1H$ NMR spectra of the skin samples with different treatments are found to be different in both the aromatic and aliphatic regions. In general, the intensities of most resonances are significantly reduced in the ZnO lotion wipe treated sites. FIG. 11 shows the overlay of the aromatic regions of the $^1H$ NMR spectra from a single subject. The proton signal intensity may decrease with ZnO lotion wiping treatment (FIG. 11, spectrum B), compared with those of occluded control (FIG. 11, spectrum A) and water/preservative wipes (FIG. 11, spectrum C). These results may indicate that the ZnO wipes are efficient in removing these metabolites from skin, while water/preservative wipes appear to be less efficient.

Figure 12:
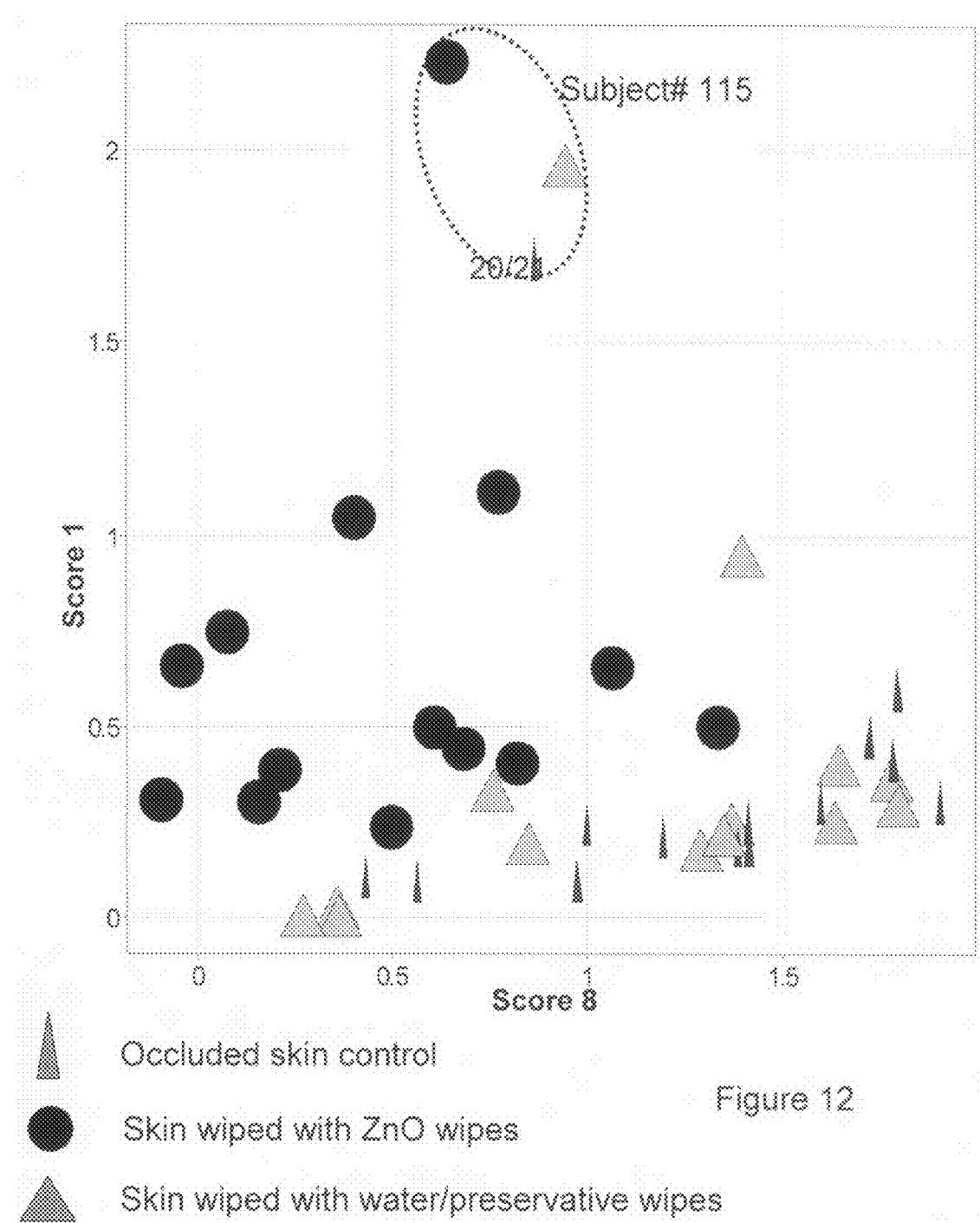
FIG. 12 shows separation of ZnO lotion wipes treated skin from vehicle (water/preservative only) wipes treated skin and occluded control skin on a two-dimensional scores plot.

MFA results are shown in FIG. 12 as a scores plot of two factors. The plot shows a separation of ZnO lotion wipes treatment from both occluded control and water/preservative wipes.

Individual variation is observed in FIG. 12 and results for subject #115 appear to be an outlier. In examining the loading of Factor 1, lactic acid, one of the major metabolites that is often used as a marker for sweat gland activity, is identified as responsible for Subject #115's shift away from the rest of the subjects. This may become clearer by displaying the scores plot in a 3D format (FIG. 13A) using an additional factor. It is not surprising to find Subject #115 positioned separately from the rest of the group in a 2D plot of Factor 1, with a high score on Factor 1.

Figure 13B:
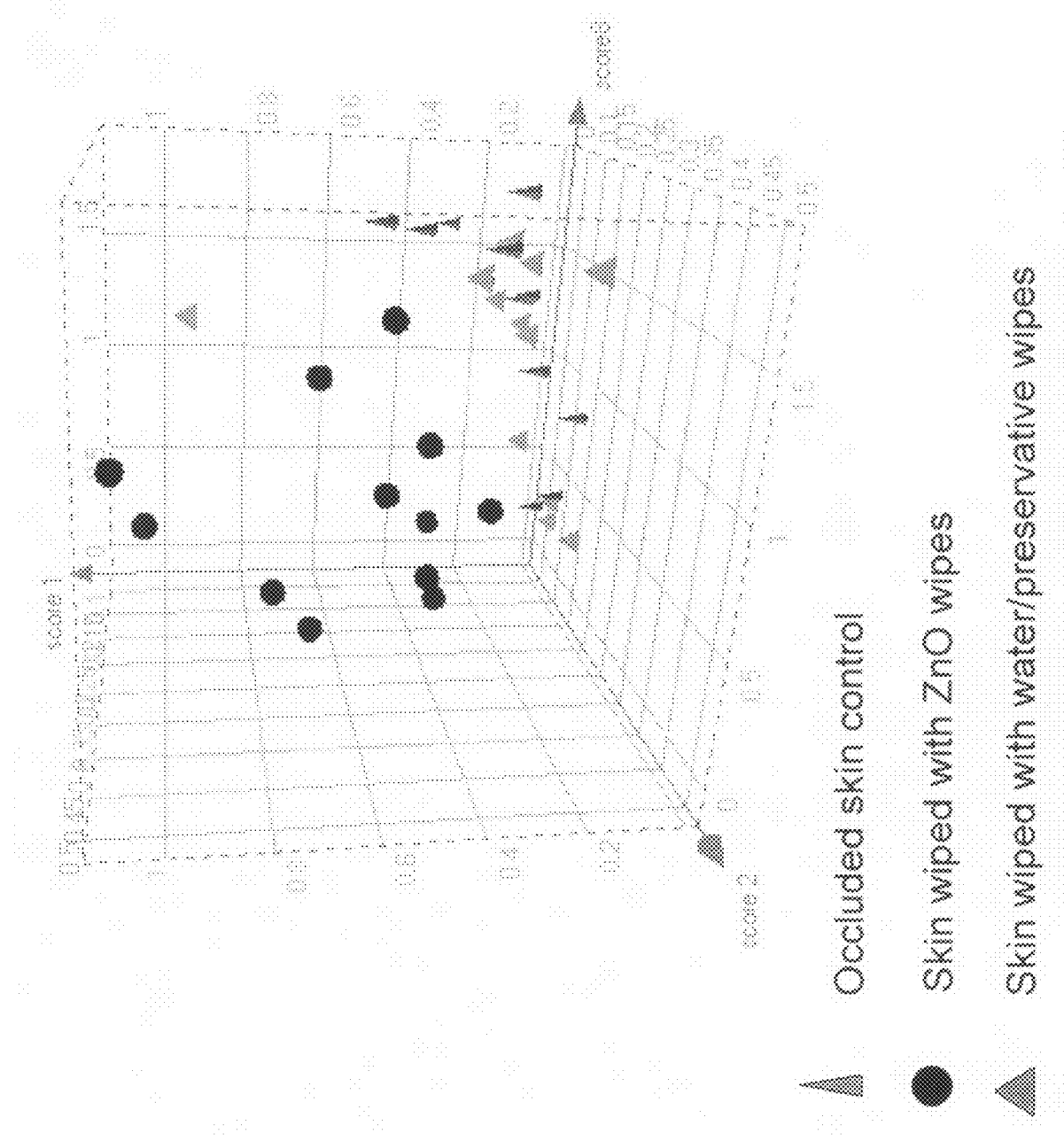
FIG. 13B shows an expanded plot of the three-dimensional scores plot of FIG. 13A and is shown without subjects #113 and #115.

As indicated in FIG. 13B, which represents a high resolution expansion of FIG. 13A, a skin response to ZnO wipes may be separated from occluded skin and vehicle (water/preservative only) wipes. The separation between occluded skin and ZnO wipe treated skin may suggest unique biomarker presentation on the subject's skin as the result of the occlusion and wipes treatments. Individual variations in skin may be recognized as a major cause for poor clinical results based on conventional methods such as visual grading and TEWL. However, results from the skin metabonomics show that the skin conditions caused by either individual variations or skin treatments can be resolved, even when the individual variation is far greater than skin responses to the treatments.

Results from other skin treatments (C, D and F, defined above) may show similar responses as their wipes counterparts. Skin samples treated with ZnO lotion wipes are distinguishable from both vehicle (water/preservative) wipes and occlusion control. The ZnO lotion wipe cleaning effect can be seen by overlaying individual $^1$H NMR spectra from different treatments through multivariate data analysis. The grouping of skin samples with each treatment after the multivariate analysis may indicate metabolic differences. The differences are not caused by lotion residues.

The foregoing describes and exemplifies the invention but is not intended to limit the invention defined by the claims which follow. All of the arrays and/or methods disclosed and claimed herein can be made and executed without undue experimentation in light of the present disclosure. While the materials and methods of this invention have been described in terms of specific embodiments, it will be apparent to those of skill in the art that variations may be applied to the materials and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those of ordinary skill in the art are deemed to be within the spirit, scope and concept of the invention as defined by the appended claims.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflict with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A method to assess skin condition comprising the steps of:
    extracting biomarkers from a tape strip collected from a human skin sample;
    obtaining an NMR spectrum for the extracted biomarkers;
    analyzing the NMR spectrum using a pattern recognition technique; and
    evaluating the pattern recognition technique result for patterns consistent with a skin state.

2. The method of claim 1, wherein the skin state is selected from the group consisting of topically challenged, therapeutically challenged, prophylactically challenged, soiled, clean, non-occluded, partially occluded, and fully occluded.

3. The method of claim 1, further comprising applying orthogonal signal correction to the NMR spectrum.

4. The method of claim 1, further comprising evaluating the NMR spectrum for the presence, absence, or relative abundance of a known biomarker associated with a skin state.

5. The method of claim 4, wherein the known biomarker is urocanic acid.

6. The method of claim 1, wherein one or more unidentified biomarkers is associated with the skin state.

7. The method of claim 1, wherein the extraction step selects for water-soluble biomarkers.

8. The method of claim 1, wherein the method is repeated for the same skin sample at different time points.

9. The method of claim 1, wherein the method is repeated using biomarkers obtained from different depths of the stratum corneum of the same skin sample.

10. A method for establishing biomarker patterns consistent with a given skin state comprising the steps of:
    extracting first biomarkers from a tape strip collected from a human skin sample having a first know skin state;
    obtaining a first NMR spectrum for the first extracted biomarkers;
    analyzing the first NMR spectrum using a pattern recognition technique;
    evaluating the pattern recognition technique results for the first extracted biomarkers for patterns;
    extracting second biomarkers from a tape strip collected from a human skin sample having a second known skin state different from the first known skin state;
    obtaining a second NMR spectrum for the second extracted biomarkers;
    analyzing the second NMR spectrum suing a pattern recognition technique;
    evaluating the pattern recognition technique results for the second extracted biomarkers for patterns; and comparing the pattern recognition technique results for the first and second extracted biomarkers to identify pattern differences associated with one or more known skin states.

11. The method of claim 10 wherein each of the known skin states is selected from the group consisting of topically challenged, therapeutically challenged, prophylactically challenged, soiled, clean, non-occluded, partially occluded, and fully occluded.

12. The method of claim 10 wherein one or more unidentified biomarkers is associated with the first or second know skin state.

13. The method of claim 10 further comprising applying orthogonal signal correction to the first or second NMR spectrum.

14. The method of claim 10 further comprising:
extracting third biomarkers from a tape strip collected from a human skin sample having a third skin state;
obtaining a third NMR spectrum for the third extracted biomarkers;
analyzing the third NMR spectrum using a pattern recognition technique;
evaluating the pattern recognition technique results for the third extracted biomarkers for patterns; and
comparing the pattern recognition technique results for the first, second, and third extracted biomarkers to identify pattern differences associated with one or more known skin states.

15. The method of claim 1, further comprising a step of treating the skin sample.

16. The method of claim 15, wherein the skin is treated before extracting a set of biomarkers.

17. The method of claim 16, wherein the treatment is selected from intentional occlusion, a dry wipe, a wet wipe, a lotion, and water.

* * * * *

UNITED STATES PATENT AND TRADEMARK OFFICE
CERTIFICATE OF CORRECTION

PATENT NO. : 7,761,242 B2
APPLICATION NO. : 11/707670
DATED : July 20, 2010
INVENTOR(S) : Honkonen et al.

It is certified that error appears in the above-identified patent and that said Letters Patent is hereby corrected as shown below:

Column 12
Line 64, delete "(—H₃)" and insert --(-CH₃)--.

Column 15
Line 50, delete "(3—24—t)" and insert --(3—24—f)--.

Column 20
Line 52, delete "know" and insert --known--.
Line 64, delete "suing" and insert --using--.

Column 21
Line 11, delete "know" and insert --known--.

Signed and Sealed this
Fifteenth Day of March, 2011

David J. Kappos
*Director of the United States Patent and Trademark Office*